US009637515B2

(12) United States Patent
Ahmad et al.

(10) Patent No.: US 9,637,515 B2
(45) Date of Patent: May 2, 2017

(54) GUGGULPHOSPHOLIPID METHODS AND COMPOSITIONS

(75) Inventors: Moghis U. Ahmad, Wadsworth, IL (US); Shoukath M. Ali, Vernon Hills, IL (US); Ateeq Ahmad, Wadsworth, IL (US); Saifuddin Sheikh, Waukegan, IL (US); Imran Ahmad, Libertyville, IL (US)

(73) Assignee: JINA PHARMACEUTICALS, INC., Libertyville, IL (US)

( * ) Notice: Subject to any disclaimer, the term of this patent is extended or adjusted under 35 U.S.C. 154(b) by 2201 days.

(21) Appl. No.: 12/513,654

(22) PCT Filed: Nov. 6, 2007

(86) PCT No.: PCT/US2007/083832
§ 371 (c)(1),
(2), (4) Date: Feb. 2, 2010

(87) PCT Pub. No.: WO2008/058156
PCT Pub. Date: May 15, 2008

(65) Prior Publication Data
US 2010/0151002 A1 Jun. 17, 2010

Related U.S. Application Data

(60) Provisional application No. 60/856,952, filed on Nov. 6, 2006.

(51) Int. Cl.
| | | |
|---|---|---|
| *A61K 9/127* | (2006.01) | |
| *C07J 13/00* | (2006.01) | |
| *C07J 7/00* | (2006.01) | |
| *C07J 31/00* | (2006.01) | |
| *C07J 41/00* | (2006.01) | |
| *C07J 51/00* | (2006.01) | |
| *A61K 48/00* | (2006.01) | |

(52) U.S. Cl.
CPC .......... *C07J 13/007* (2013.01); *C07J 7/0005* (2013.01); *C07J 31/006* (2013.01); *C07J 41/0005* (2013.01); *C07J 51/00* (2013.01)

(58) Field of Classification Search
USPC ....................................................... 424/450
See application file for complete search history.

(56) References Cited

U.S. PATENT DOCUMENTS

| | | | |
|---|---|---|---|
| 3,053,834 A | 9/1962 | Fried | |
| 3,141,028 A | 7/1964 | Benn | |
| 3,141,029 A | 7/1964 | Ringold et al. | |
| 4,221,787 A | 9/1980 | Bodor et al. | |
| 5,415,869 A | 5/1995 | Straubinger | |
| 5,690,948 A | 11/1997 | McCook et al. | |
| 5,709,879 A * | 1/1998 | Barchfeld et al. | 424/450 |
| 6,063,776 A * | 5/2000 | Ostlund, Jr. | 514/182 |
| 6,126,965 A | 10/2000 | Kasid | |
| 6,303,378 B1 | 10/2001 | Bridenbaugh et al. | |
| 6,383,514 B1 * | 5/2002 | Weitkemper et al. | 424/456 |
| 6,933,291 B2 * | 8/2005 | Qi et al. | 514/171 |
| 2005/0288244 A1 | 12/2005 | Manoharan et al. | |
| 2006/0035871 A1 * | 2/2006 | Auweter et al. | 514/169 |
| 2006/0069070 A1 | 3/2006 | Fiorucci et al. | |

FOREIGN PATENT DOCUMENTS

| | | |
|---|---|---|
| WO | WO00/01366 | 1/2000 |
| WO | WO02/32400 | 4/2002 |
| WO | WO02/058622 | 8/2002 |
| WO | WO03/018018 | 3/2003 |
| WO | WO03/030864 | 4/2003 |
| WO | WO2004/094450 | 11/2004 |
| WO | WO2006/017211 | 2/2006 |

OTHER PUBLICATIONS

Urizar et al., Ann Rev Nutr, 2003, 23: 303-313.*
Sobel et al. J., Am. Chem. Soc.,1941 63: 1259-1261.*
Achenbach, H. et al., "Cholestane- and Pregnane-Type Glycosides from the Roots of Tribulus Cistoides," Phytochemistry, 1996, 41, pp. 907-917.
Benn, Walter and Dodson, R.M., "The Synthesis and Stereochemistry of Isomeric 16-Hydroxy-17 (20)-pregnenes," J Organic Chemistry, 1964, 29, pp. 1142-1148.
Matsuda, Hisashi, et al., "Absolute stereostructures of polypodane- and octanordammarane-type triterpenes with nitric oxide production inhibitory activity from guggul-gum resins," Bioorganic Medicinal Chem, 2004, 12, pp. 3037-3046.
U.S. Appl. No. 60/850,446, filed Oct. 10, 2006, Ali.
Andresen, et al. "Enzymatic release of antitumor ether lipids by specific phospholipase A2 activation of liposome-forming prodrugs" J. Med. Chem. 2004, 47, 1694-1703.
Andresen, et al. "Synthesis and biological activity of anticancer ether lipids that are specifically released by phospholipase A2 in tumor tissue" J. Med. Chem. 2005, 48, 7305-7314.
Bowlby, M.R. "Pregnenolone sulfate potentiation of N-methyl-D-aspartate receptor channels in hippocampal neurons" Mol. Pharmacol. 1993, 43,813.
Browne, et al. "Preparation of phospholipid analogues using the phosphoramidite route" J. Chem. Soc. Perkin Trans. 1. 2000, 653-657.

(Continued)

*Primary Examiner* — Ileana Popa
(74) *Attorney, Agent, or Firm* — Casimir Jones, S.C.; Mary Ann Brow

(57) ABSTRACT

The present invention relates to the methods for preparing synthetic guggulphospholipids, their fatty acid analogues and other bioactive molecules. The present invention relates to E-guggulsterone and Z-guggulsterone or mixture of E- and Z-guggulsterones. The present invention also provides a novel method for the preparation of E-guggulsterol and Z-guggulsterol or mixture of E- and Z-guggulsterols from a mixture of E- and Z-guggulsterones. The present invention further relates to guggulphospholipids and other bioactive molecules incorporated into complexes such as liposomes, complexes, emulsions, vesicles, micelles, and mixed micelles, which can include other active agents, such as hydrophobic or hydrophilic drugs for use, e.g., in treatment of human and animal diseases.

14 Claims, 9 Drawing Sheets

(56) References Cited

OTHER PUBLICATIONS

Bruzik, et al. "General Synthesis of Phosphatidylinositol 3-Phosphates" Tet. Lett. 1995, 36, 2415-2418.

Chen, et al. "Asymmetric Total Synthesis of Phosphatidylinositol3-Phosphate and 4-Phosphate Derivatives" J. Org. Chem. 1998, 63, 6511-6522.

Chevallier, et al. "Rapid access to synthetic lysobisphosphatidic acids using P(III) chemistry." Org. Lett. 2000, 2, 1859-1861.

Dreef, et al. "Synthesis of 1-O-(1,2-Di-O-Palmitoyl-Sn-Glycero-3-Phospho)-D-MYO-Inositol 4,s-Bisphosphate: An Analogue of Naturally Occurring (Ptd)Ins(4, 5)P2" Tetrahedron Lett 1988, 29, 6513-6516.

Drummond, et al. "Optimizing liposomes for delivery of chemotherapeutic agents to solid tumors" D. Pharm. Rev., 1999, 51, 691-743.

Flood, et al. "Memory-enhancing effects in male mice of pregnenolone and steroids metabolically derived from it." Proc. Natl. Acad. Sci. USA 1992, 89, 1567.

Greene, et al. Protective Groups in Organic Synthesis, 3rd edition, John Wiley & Sons, New York (1999).

Gujral, et al. "Antiarthritic and anti-inflammatory activity of gum guggul (*Balsamodendron mukul* Hook" Ind. J Physiol. Pharmacol. 1960, 4, 267.

Hunt, et al. "Oxidative glycation and free radical production: a causal mechanism of diabetic complications" Free Radical Res. Commun. 1991,12-13,115.

Lindberg, et al. "Efficient synthesis of phospholipids from glycidyl phosphates" P. J. Org. Chem. 2002, 67, 194-199.

Malet-Martino, et al. "The prodrugs of 5-fluorouracil" Curr. Med. Chem.-Anti-Cancer Agents, 2002, 2, 267-310.

Martin, et al. "General Method for the Synthesis of Phospholipid Derivatives of 1,2-O-Diacyl-sn-glycerols" J. Org. Chem., 1994, 59, 4805-4820.

Marx, et al. "Synthesis and evaluation of neoplastic cell growth inhibition of 1-N-alkylamide analogues of glycero-3-phosphocholine." J. Med. Chem. 1988, 31, 858-863.

Murakami, et al. "An Efficient Synthesis of Unsymmetrical Optically Active Phosphatidyl Glycerol" J. Org. Chem. 1999, 64, 648-651.

Nityanad, et al. "Cholesterol lowering activity of the various fractions of the guggal" Ind J Exp.Biol.1973, 11, 395.

Patil, et al. "Chemistry of Ayurvedic Crude Drugs" Tetrahedron, 1972, 28, 2341-52.

Prestwich, et al. "Tethered IP3 Synthesis and Biochemical Applications of the 1-O-(3-Aminopropyl) Ester of Inositol 1,4,5-Trisphosphate" J. Am. Chem. Soc. 1991, 113, 1822-1825.

Satyavati, G.V. "Guggulipid: a Promising Hypolipidaemic Agent from Gum Guggul" Economic and Medical Plant Research. 1991, 5, 47.

Singh, et al. "Guggulsterone, a Potent Hypolipidaemic, Prevents Oxidation of Low Density Lipoprotein" Phytotherapy Research, 1997, 11,291-4.

Watanabe, et al. "Protection of Phosphate with the 9-Fluorenylmethyl Group. Synthesis of Unsaturated-acyl Phosphatidylinositol. 4,5-Bisphosphate" Tetrahedron Lett. 1997, 38, 7407-7410.

Watanabe, et al. "Synthesis of dipalmitoyl-phosphatidylinositol 5-phosphate and its modified biological tools" Tetrahedron Lett. 2000, 41, 8509-8512.

Watanabe, et al. "Phosphonium Salt Methodology for the Synthesis of Phosphoric Monoesters and Diesters and its Application to Selective Phosphorylation" Tetrahedron Lett. 1993, 34, 497-500.

Wilk, et al. "N-Trifluoroacetylamino Alcohols as Phosphodiester Protecting Groups in the Synthesis of Oligodeoxyribonucleotides" J. Org. Chem. 1997, 62, 6712-6713.

Wissner, et al. "Analogues of platelet activating factor. 5. Multiple oxygen substitution of the alkoxy chain." J. Med. Chem. 1986, 29, 1315-1319.

\* cited by examiner

GUGGULPHOSPHOLIPID METHODS AND COMPOSITIONS

This application is a national stage application under 35 U.S.C. §371 of International Application PCT/US07/83832, filed Nov. 6, 2007, which claims priority to U.S. Provisional Application Ser. No. 60/856,952, filed Nov. 6, 2006, which is incorporated herein by reference.

FIELD OF THE INVENTION

This invention relates to synthesis of novel phospholipid analogues and variants of E- and Z-guggulsterones or guggulsterols or mixtures of E- and Z-guggulsterones or E- and Z-guggulsterols, and their target delivery for the treatment of human and animal diseases.

BACKGROUND OF THE INVENTION

Ayurveda practitioners take a holistic view of human disease. It views any disease as a dysfunction of the whole body rather than of a single organ or physiological process. Most of the Ayurvedic drugs therefore are likely to act on a number of dysfunctions of the body involving a number of organs and functions. In the 1960s the oleogum resin (gum guggul), isolated from a small tree *Commiphora wighitii* belonging to the family Burseraceae, was studied for its potential use in the treatment of elevated blood cholesterol or hyperlipidemia. The *Commiphora* tree, in general, is mentioned in the classic Ayurvedic literature for use in the treatment of bone fractures, arthritis, obesity, inflammation, cardiovascular diseases and lipid disorders. With the discovery of the hypolipidemic activity for the gum guggul, several chemical investigations were undertaken and found that gum guggul is a complex mixture of various classes of chemical compounds such as linans, lipids, diterpenoids, and plant steroids. Based on the structure function analysis of gum guggul, it was determined that the soluble portion of the gum in ethyl acetate, and specifically its neutral portion, contained most of the hypolipidemic properties. The neutral fraction was found to be source of sterol compounds known as Z- and E-guggulsterone, present in an amount minimum of 2.5% and responsible for lowering of blood cholesterol [Indian Pharmacopea, 1988; G. V. Satyavati, *Economic and Medical Plant Research.* 5, 47 (1991)].

Modern pharmacological studies on the crude drug and some of its fraction have supported the claims of Ayurveda. The anti-arthritis and anti-inflammatory activities were confirmed by Gujral et al. [M. L. Gujral, K. Sareen, K. K. Tangri, M. K. P. Amma, and A. K. Roy, *Ind. J Physiol. Pharmacol.* 4, 267 (1960)]. A mixed type of mechanism has been implicated for lipid lowering effect of gum guggul. The stimulation of plasma LCAT, hepatic lipases, receptor mediated catabolism of LDL and increased faecal bile acid excretion as well as suppression of hepatic cholesterol biosynthesis are the mechanisms responsible for lipid lowering effect of gum guggul [S, Nityanand and N. K. Kapoor, *Ind J Exp. Biol.* 11, 395 (1973); N. K. Kapoor and S, Nityanand, *Ind. J Heart Res. Supp*-1.22 (1988)]. With the discovery of the hypolipidemic activity for the gum resin, systemic chemical investigations were carried out to characterize compounds of the gum resin responsible for hypolipidemic activity. Mc Cook et al. have claimed alcoholic extract of gum guggul for controlling or preventing sebum secretion from sebocytes which is associated with a shiny, undesirable appearance and a disagreeable tactile sensation [J. P. Mc Cook et al. U.S. Pat. No. 5,690,948 (1997)].

As is already known, cholesterol is the precursor of neurosteroid pregnenlone. Similarity among biogenic precursor of pregnenolone and guggulsterones or guggulsterol [V. D. Patil, U. R. Nayak, and Sukh Dev, *Tetrahedron* 28, 2341 (1972)] has prompted exploration of the properties of synthetically pure pharmaceutically active novel phospholipid bonded to guggulsterone or guggulsterol. Behavioral studies have suggested a potential role of pregnenolone for memory enhancement. Intracerebroventricular (i.c.v) administration of pregnenolone and pregnenolone sulfate leads to amelioration in various memory tasks in rodents [J. F. Flood, J. F. Moorley, and E. Robert. *Proc. Natl. Acad. Sci. USA* 89, 1567 (1992)]. These memory-enhancing effects might be attributed to the N-methyl-D-aspartate (NMDA)-antagonistic properties of pregnenolone sulfate since NMDA agonists have been shown to impair cognitive functions in rodents [M. R. Bowlby, *Mol. Pharmacol.* 43, 813 (1993)].

In recent years, interest is increasing to understand the role of free radical oxidative damage in human diseases. Free radicals are highly reactive species that have the potential to oxidize biological membranes including proteins, lipids and DNA. To prevent or reduce oxidation, rich arrays of natural antioxidant mechanism exist. These antioxidant defense mechanisms have been found defective in many diseases. Increased production of free radicals has been strongly implicated in the pathophysiology of diabetes and atherosclerosis. Glucose combines with serum proteins and lipoproteins in a non-enzymatic glycation reaction and may auto oxidize in situ, generating free radicals and causing local oxidative damage [J. V. Hunt and S. P. Wolff, *Free Radical Res. Commun.* 12-13, 115 (1991)]. The free radical scavenging antioxidants react preferentially with free radicals before vital structure can be attacked. The gum guggul and E- and Z-guggulsterones are also known as to have antioxidant property [K. Singh, R. Chander, and N. K. Kapoor, *Phytotherapy Research,* 11, 291 (1997)].

The guggulphospholipid methods and compositions of the present invention find application in each of these areas.

SUMMARY OF THE INVENTION

The present invention relates to novel guggulphospholipid compositions and methods of synthesis and uses thereof. In some embodiments, the invention pertains to synthetic, pharmaceutically active phospholipids conjugated with E-guggulsterone and Z-guggulsterone or guggulsterols, or mixture of E-guggulsterone and Z-guggulsterone or mixture of E-guggulsterol and Z-guggulsterol and their analogues. Phospholipids are generally used for drug delivery. The guggulphospholipids and other bioactive products of the present invention help to target delivery of novel products, with or without additional therapeutically active products, for the treatment of human or animal diseases, such as prevention and treatment of abnormal cell growth, cancer, cardiovascular disease, viral infection, skin infections, memory loss, obesity, proliferation in inflammation, etc.

The compositions of the present invention find use, for example, in the prevention and treatment of abnormal cell growth, proliferation in inflammation, lowering the elevated low density lipoprotein (LDL) and high levels of cholesterol, and elevating the low levels of the high density lipoprotein (HDL), neoplastic and cardiovascular diseases in humans and animals. This invention also provides methods of using the disclosed compositions for preventing or controlling cognitive dysfunction, hyperglycemia and skin infection.

In some embodiments, the present invention comprises guggul derivatives having general structures III-XII, as diagrammed in FIG. 1. In some embodiments, of structures III and IV, $R_1$ is a saturated or unsaturated acyl or alkyl groups having between 1 and 34 carbon atoms. In some embodiments, the guggul derivative comprises structure IV, and $R_1$ is a sugar. In some embodiments, the guggul derivative comprises structure V, wherein $R_1$ and $R_2$ are same or different and at least one of the $R_1$ or $R_2$ is a saturated or unsaturated acyl group or alkyl group having between 1 and 34 carbon atoms.

In some embodiments of guggul derivatives comprising structures IV-X, side group X is hydrogen, methyl, ammonium, sodium, potassium, calcium, barium ion or any non-toxic ion.

In some embodiments of a guggul derivative comprising structures VI, X and Y are the same or different, and are hydrogen, methyl, hydrogen, ammonium, sodium, potassium, calcium, barium ion or any non-toxic ion.

In some embodiments of a guggul derivative comprising structure VIII, $R_3$, $R_4$ and $R_5$ are the same or different, and are hydrogen or methyl group. Formula VIII is a cationic guggul derivative when X is a methyl group.

In some embodiments of a guggul derivative comprising structure X, PEG (polyethylene glycol) is a long chain, linear or branched synthetic polymer composed of ethylene oxide units, $HO(CH_2CH_2O)_n$ $CH_2CH_2OCH_3$, where n is typically between about 1 and about 1000.

In some embodiments of guggul derivative comprising structure XI, the drug is an active agent.

Formula XII is a cationic guggul derivative, wherein $R_6$, $R_7$, and $R_8$ are the same or different and are hydrogen, methyl, alkyl, substituted alkyl, alkyoxy, substituted alkyloxy groups, are optionally hydroxylated, aminated, and/or polyaminated, the guggul derivative having overall positive charge.

In some embodiments, guggul derivatives comprising structures III-XII are in a form selected from the group consisting of E-isomers, Z-isomers, or a mixture of E and Z isomers.

In some embodiments, guggul derivatives having structures III-XII are optically pure, while in some embodiments, the structures III-XII are mixtures of optical isomers.

In some embodiments, the present invention provides methods of preparing guggul derivatives of formula III-XII from guggulsterol having structure IIA.

In some embodiments, the guggulsterol IIA is an E-isomer, while in other embodiments, it is a Z-isomer, while in still other embodiments, it is a mixture of E and Z isomers. In some embodiments the guggulsterol is optically pure, while in some embodiments, the guggulsterol is a mixture of optical isomers. The present invention also provides methods of preparing guggulsterol IIA from guggulsterone I.

In some embodiments, the present invention provides methods of preparing guggul derivatives of formula III-XII from guggulsterone having structure I (shown in FIG. 2). In some embodiments, the guggulsterone I is an E-isomer, while in other embodiments, it is a Z-isomer, while in still other embodiments, it is a mixture of E and Z isomers.

In some embodiments of the methods of synthesizing a guggul derivative from a guggulsterol IIA or a guggulsterone I, the guggul derivatives (III-XII) are synthesized from the precursor in a single step, while in some embodiments, the guggul derivatives are synthesized in a sequence of multiple steps.

In some embodiments, the guggulsterol is prepared in a single step or a sequence of many steps, while in some embodiments, the guggulsterol is obtained, e.g., commercially.

In some embodiments of the methods of preparing compounds of formulas IV-VI, VIII-X, at least one step comprises the use of phosphoramidite reagent or a phosphorylating agent. In some preferred embodiments, the phosphoramidite reagent includes but not limited to N,N-diisopropylmethylphosphoramidic chloride, (benzyloxy)(N,N-diisopropylamino)chlorophosphine, benzyloxybis(diisopropylamino)phosphine, 2-cyanoethyl-N,N,N,N-tetraisopropylphosphoramidite, (2-cyanoethyl)(N,N-diisopropylamino)chlorophosphine, difluorenyl diisopropylphosphoramidite, methyl-N,N,N,N tetraisopropylphosphorodiamidite, dimethyl N,N-diisopropylphosphoramidite, dibenzyl diisopropylphosphoramidite, di-tert-butyl-N,N-diisopropylphosphoramidite, 2-(diphenylmethylsilyl)ethyl-N,N,N,N-tetraisopropylphosphoramidite, (N-trifluoroacetylamino)butyl and (N-trifluoroacetylamino pentyl-N,N,N,N-tetraisopropylphosphoramidites. In some embodiments, the phosphorylating agent includes but is not limited to 2-bromoethyldichlorophosphate, trimethylsilylethyl dichlorophosphate, methyl dichlorophosphate, 2-chloro-2-oxo-1,3,2-dioxaphospholane, 2-chlorophenyl dichlorophosphate, and phosphorus oxychloride.

In some embodiments of the methods of the present invention, structure XI is prepared by conjugating guggulsterol with a drug, e.g., directly or through a linker. In some embodiments in which a linker is used, the linker is an alkyl group, which is optionally substituted with functional groups such as carbonyl, carboxyl, carbonate, amino, amide, ester, thioester groups, succinate, glutarate, carbamate, ether; phosphate; phosphonate, diphosphate; pyrophosphate; and the like.

In some embodiments, the methods of the present invention comprise formation of complexes including but not limited to liposomes, wherein the liposomes or complexes comprise guggul derivatives III-XII. In some preferred embodiments, the complexes are micelles, vesicles, or emulsions. In some embodiments, the methods of the present invention comprise formation of a composition comprising a plurality of micelles, wherein the micelles are in the form of monomeric, dimeric, polymeric or mixed micelles.

In some embodiments, the present invention comprises a method of retaining drug in liposomes or complexes, comprising preparing guggul derivatives by the methods described herein, and including the guggul derivatives and a drug in a liposome or complex. In some embodiments, the present invention comprises a liposomal composition prepared as described above.

In some embodiments, the present invention comprises a method of complexing a drug with a guggul derivative III-XII. In some embodiments, the guggul derivative is in a complex prior to complexing with the drug.

In some embodiments, the invention comprises any of the methods described above, wherein the complexes includes, micelles, mixed micelles, polymeric micelles, vesicles, emulsions and liposomes.

In some embodiments of the present invention, the compositions of the methods described above further comprise phospholipids, pegylated phospholipids, polyethylene glycol (PEG), fatty acids, sterols, cholic acid, or a tocopherol. In some embodiments, the cholic acid is sodium deoxycholate. In some preferred embodiments comprising the use of PEG, the PEG has an average molecular weight of 200-20,000. In embodiments comprising fatty acids, in some embodiments, at least one of the fatty acids is selected from a group consisting of fatty acids having chain length of $C_4$-$C_{34}$. In some embodiments, at least one of the fatty acids is saturated, while in some embodiments, at least one of the fatty acids is unsaturated.

In some embodiments, at least one fatty acid is in acidic form, while in other embodiments; at least one fatty acid is in salt form.

In certain preferred embodiments, at least one of the phospholipids comprises a phosphatidylcholine, a phosphatidylethanolamine, a phosphatidylglycerol, a phosphatidylserine, a phosphatidylinositol, a phosphatidic acid. In particularly preferred embodiments, at least one of said phosphatidylcholine is dimyristoylphosphatidylcholine, disteroylphosphatidylcholine, dipalmitoylphosphatidylcholine, dioleoylphosphatidycholine, diarachidonoylphosphatidylcholine, egg phosphatidylcholine, soy phosphatidylcholine, hydrogenated soy phosphatidylcholine, partially hydrogenated soy phosphatidylcholine, or a mixture thereof. In additional preferred embodiments, at least one of said phosphatidylethanolamine is dimyristoylphosphatidylethanolamine, disteroylphosphatidylethanolamine, dipalmitoylphosphatidylethanolamine, dioleoylphosphatidyethanolamine, diarachidonoylphosphatidylethanolamine, egg phosphatidylethanolamine, or a mixture thereof.

In some embodiments, at least one of said phosphatidylglycerol is dimyristoylphosphatidylglycerol, disteroylphosphatidylglycerol, dipalmitoylphosphatidylglycerol, dioleoylphosphatidylglycerol, diarachidonoylphosphatidylglycerol, or a mixture thereof.

In some embodiments, at least one of said phosphatidylserine is dimyristoylphosphatidylserine, disteroylphosphatidylserine, dipalmitoylphosphatidylserine, dioleoylphosphatidylserine, diarachidonoylphosphatidylserine, or a mixture thereof.

In some embodiments, at least one of said phosphatidylinositol is dimyristoylphosphatidylinositol, disteroylphosphatidylinositol, dipalmitoylphosphatidyinositol, dioleoylphosphatidylinositol, diarachidonoylphosphatidylinositol, or a mixture thereof.

In some embodiments, at least one of said phosphatidic acid is dimyristoylphosphatidic acid, disteroylphosphatidic acid, dipalmitoylphosphatidic acid, dioleoylphosphatidic acid, diarachidonoylphosphatidic acid or a mixture thereof.

In some embodiments, at least one of said pegylated phospholipids comprises a pegylated derivative of phospholipids selected from the group consisting of pegylated derivatives of disteroylhosphatidylglycerol, dimyristoylhosphatidylglycerol, and dioleoylphosphtidylglycerol.

In some embodiments, the structure XI is prepared by conjugating a guggulsterol with a drug directly or through a linker, and the composition further comprises a sterol selected from a group consisting of cholesterol, derivatives of cholesterol, cholesteryl sulfate, cholesterol succinate, cholesterol hemisuccinate, cholesterol oleate, cortisol, corticosterone, hydrocortisone, cholesterol-PEG, coprostanol, cholestanol, cholestane, β-sitosterol, lanosterol, campesterol, lathosterol, stigmasterol, stigmastanol, calciferol, or a mixture thereof.

In some embodiments of the methods and compositions of the present invention, the composition comprises at least one drug and the at least one drug is a therapeutically active agent. In some preferred embodiments, at least one therapeutically active agent comprises an anticancer drug, while in some preferred embodiments; at least one therapeutically active agent comprises an antiviral drug. In yet more preferred embodiments, at least one therapeutically active agent comprises an antifungal drug.

In preferred embodiments of the methods and compositions of the present invention, at least one of said therapeutically active agents is to treat a condition selected from the group consisting of cardiovascular disease, neoplasia, memory loss, inflammation, anti-inflammation drug, skin infection or skin disease, serum cholesterol level, and hyperglycemia. In some preferred embodiments, at least one of said therapeutically active agents improves cognitive function.

In some embodiments of the methods and compositions of the present invention, the composition comprises a liposome composition comprising unilamellar vesicles, multilamellar vesicles, or mixtures thereof. In some embodiments, the liposomes or any of the complexes described herein have an overall negative charge, while in some embodiments they have an overall positive charge. In some embodiments, they have an overall neutral charge.

In some embodiments of the methods and compositions of the present invention, the composition comprises a liposome or complex composition, wherein the liposome or complex has a mean diameter of about 20 micron or less. In some preferred embodiments, the liposome or complex has a mean diameter of about 10 micron or less, while in some preferred embodiments, the liposome or complex has a mean diameter of about 5 micron or less. In some particularly preferred embodiments, the liposome or complex has a mean diameter of about 1 micron or less, 500 nm or less, 200 nm or less, in still more preferred embodiments, 100 nm or less.

In some embodiments of the methods and compositions of the present invention, the composition is in lyophilized form. In some embodiments, the lyophilized composition further comprises a cryoprotectant such as one or more sugars. In preferred embodiments, the cryoprotectant is a sugar selected from a group consisting of trehalose, maltose, lactose, sucrose, and dextran.

In some embodiments of the methods and compositions of the present invention, the liposome or complex composition comprising one or more guggul derivatives is in form selected from the group consisting of a powder form, a solution form, a suspension form, an emulsion form, a micelle form, a gel form, or a paste form.

In some embodiments, a liposome or complex composition according to the present invention is encapsulated in a capsule. In preferred embodiments, the capsule comprises an enteric coating. "Enteric" refers to the small intestine, therefore "enteric coating" generally refers to a coating that substantially prevents release of a medication before it reaches the small intestine. While not limiting the invention to any particular mechanism of action, it is understood that most enteric coatings work by presenting a surface that is stable at acidic pH but breaks down rapidly at higher pH.

In some embodiments, the present inventions comprise a method of treating a cell with a composition comprising a guggul derivative composition as described herein, comprising preparing a composition as described herein, and exposing the cell to the composition. In some preferred embodiments, the exposing of the cell occurs in vivo, e.g., in a patient or subject.

It is contemplated that in some embodiments, the exposing of a cell in a subject comprises oral delivery of the composition to the subject, while in other embodiments; the exposing of a cell comprises intravenous delivery of the composition to the subject. Routes of delivery of the composition to the subject that find use in the present invention include but are not limited to subcutaneous delivery, parenteral delivery, intraperitoneal delivery, rectal delivery, vaginal delivery and/or topical delivery. In some preferred embodiments, the subject is a mammal. In some particularly preferred embodiments, the mammal is human.

In some embodiments, the present invention comprises a method of treating a human or animal disease, comprising administering a therapeutically effective amount of a composition comprising a guggul derivative as described herein, and exposing the composition to a human or animal in need thereof, such that the composition is delivered to the human or animal patient.

In some embodiments, the present invention comprises a method of treating a human or animal disease, comprising administering a therapeutically effective amount of a composition comprising a liposome or complex comprising a guggul derivative as described herein, and exposing the composition to a human or animal in need thereof such that the active agent is delivered to the human or animal patient.

In some embodiments, the present invention comprises a method of alleviation of a human or animal disease, comprising administering a therapeutically effective amount of a composition comprising a guggul derivative as described herein, and exposing the composition to a human or animal in need thereof such that the composition is delivered to the human or animal patient.

In some embodiments, the present invention comprises a method of alleviation of a human or animal disease, comprising preparing a liposome or complex comprising a guggul derivative as described herein, and exposing the composition to a human or animal in need thereof such that the composition is delivered to the human or animal patient.

In some embodiments the treated animal is a mammal. In certain embodiments, the disease is a cancer disease. In certain preferred embodiments, cancer disease is selected from a group consisting of cancers of head, neck, brain, blood, bone, breast, lung, pancreas, spleen, bladder, prostate, testes, colon, kidney, uterus, ovary, skin, bone marrow, esophagus, stomach, intestine, larynx, tongue, and mouth.

In some embodiments, the disease is a viral disease. In certain preferred embodiments the viral disease is selected from a group consisting of HIV, herpes simplex viruses, human herpes virus 6, human herpes virus 7, human herpes virus 8, orthopoxviruses, ebola virus, influenza virus, tuberculosis, hepatitis A, hepatitis B, hepatitis C, hepatitis D, hepatitis E, hepatitis G, parainfluenza virus, respiratory syncytial virus, cholera, pneumonia, SARS virus, canary virus, West Nile virus (WNV), respiratory syncytial virus (RSV), dengue virus, varicella zoster virus, corona viruses, vaccinia virus, cytomegalovirus (CMV), human rhinovirus (HRV), papilloma virus (PV) and Epstein Barr viruses.

In some embodiments, the methods and compositions of the present invention are used in the treatment of a disease selected from the group consisting of fungal disease, cardiovascular disease, neoplasia, Alzheimer disease, an inflammatory disease, skin disease, hyperlipidemia disease, and a cognitive dysfunction disease.

Particular embodiments of the invention are described in this Summary, and below, in the Brief and Detailed descriptions of the invention. Although the invention has been described in connection with specific embodiments, it should be understood that the invention as claimed should not be unduly limited to such specific embodiments.

DEFINITIONS

Figure 1:
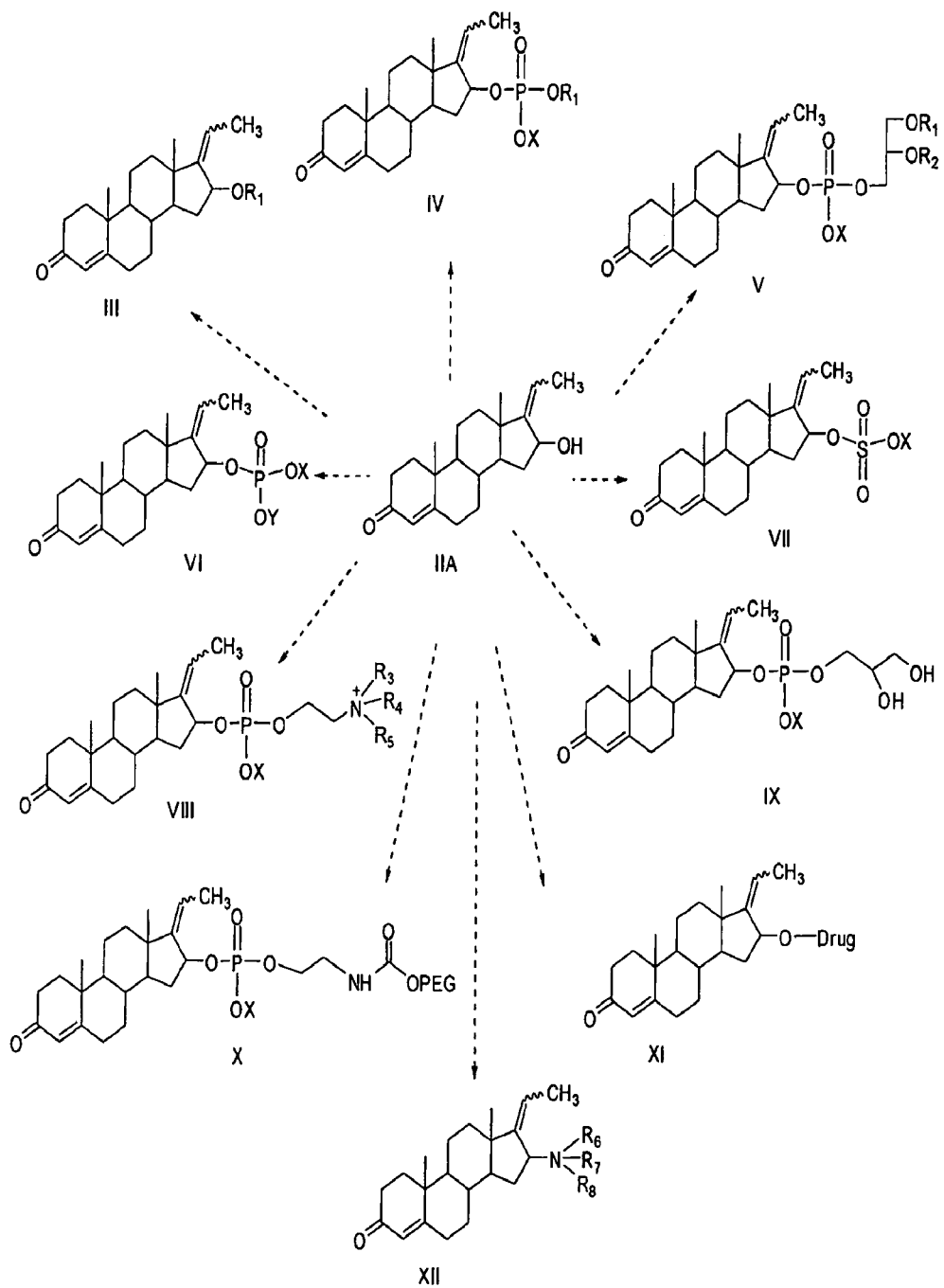
FIG. 1 diagrams compound IIA and compounds III-XII
FIG. 2 diagrams compound I and compounds IIA-IIF
FIG. 3 diagrams an exemplary synthetic scheme for compound IIA.

As used herein, the term "effective amount" refers to the amount of an active composition (e.g., a pharmaceutical compound or composition provided as a component in a lipid formulation) sufficient to effect beneficial or desired results. An effective amount can be administered in one or more administrations, applications or dosages and is not intended to be limited to a particular formulation or administration route.

As used herein, the terms "active" or "pharmaceutically active" as used in reference to an agent, composition, or compound, refers to an agent that, upon administration or application, causes a beneficial, desired, or expected result. The administration may be in one or more administrations, applications or dosages and is not intended to be limited to a particular formulation or administration route. The term is not limited to any particular level of activity.

The terms "agent" and "compound" are used herein interchangeably to refer to any atom, molecule, mixture, or more complex composition having an attributed feature. For example, an "active agent" or "active compound" refers to any atom, molecule, preparation, mixture, etc., that, upon administration or application, causes a beneficial, desired, or expected result.

As used herein, the term "administration" refers to the act of giving a drug, prodrug, or other active agent, or therapeutic treatment (e.g., compositions of the present invention) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), rectal, vaginal, oral mucosa (buccal), ear, by injection (e.g., intravenously, subcutaneously, intratumorally, intraperitoneally, etc.) and the like. Administration may be in one or more administrations, applications or dosages, and is not intended to be limited to a particular administration route.

As used herein, the term "co-administration" refers to the administration of at least two agent(s) (e.g., two separate lipid compositions, containing different active compounds) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone.

Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., an active pharmaceutical compound) with a carrier, inert or active (e.g., a phospholipid), making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be formulated for horticultural or agricultural use. Such formulations include dips, sprays, seed dressings, stem injections, sprays, and mists.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "Polyethylene glycol (PEG)" includes polymers of lower alkylene oxide, in particular ethylene oxide (polyethylene glycols) having an esterifiable hydroxyl group at least at one end of the polymer molecule, as well as derivatives of such polymers having esterifiable carboxy groups. Polyethylene glycols of an average molecular weight ranging from 200-20,000 are preferred; those having an average molecular weight ranging from 500-2000 are particularly preferred.

BRIEF DESCRIPTION OF THE INVENTION

The present invention relates to methods and compositions, and uses thereof, for the treatment of mammalian diseases. More particularly, the present invention relates to synthesis and uses of these pharmaceutically active phospholipids, their analogues and variants as described above and compositions that contain them, generally to the treatment of cholesterol lowering and weight loss, antileukemic effects, skin diseases, viral infections, as memory enhancing drug, and cancer prevention or treatment in general. The pharmaceutically active phospholipids prepared by the present method can be incorporated into liposomes, and other formulations like complexes, emulsions, vesicles, miscalls, which can also include other active agents such as hydrophobic or hydrophilic drugs. Such liposomes or lipid formulations can be used to treat human or animal diseases. Liposomes can also include ligands for targeting a particular cell type or specific tissue.

A disease may be a neoplasia, a neurodegenerative, a pulmonary disease, obesity, an inflammatory disease and a cardiovascular disease. More preferably, a neoplasia is a solid tumor, leukemia or lymphoma. More preferably, a neurodegenerative disease is Alzheimer's disease. The concept of Alzheimer's disease as an inflammatory disease has increased interest in the use of anti-inflammatory agents in improving memory loss. The present invention provides a series of novel compounds that can be useful for the treatment of neurodegenerative and other diseases mentioned above.

Animal studies have shown a positive correlation between dietary fat and the rate of tumor growth and the severity of metastases. In humans the link between nutrition and cancer is speculation, in particular the association between dietary fat and the origins of human colorectal, breast, prostatic, ovarian and endometrial cancers. It is recognized that the rate of lipid synthesis in tumor cells is quite rapid. This phenomenon can be understood, because rapidly dividing cells not only need fresh copies of DNA and proteins, but also require the security of new biomembrane composed of phospholipids and cholesterol. The cholesterol synthesizing pathway has been implicated as a promoter of tumor cell growth. The other major classes of lipids, fatty acids, are also involved in tumor cell growth. In fact many human and experimental cancers express elevated levels of fatty acid synthase (FAS), the enzyme required for endogenous fatty acid biosynthesis. As for example, a prognostic molecule isolated from a number of breast cancer patients was identified as FAS. Inhibition of FAS leads to loss of clonogenic capacity and induction of programmed cell death in Breast cancer cells. The structure of guggulsterones or guggulsterol of naturally occurring guggul resin is very similar to cholesterol. It is proposed that guggulphospholipids of the invention will mimic the cancer cells as source of phospholipids, fatty acids and cholesterol. It is proposed that the potential anti-cancer treatment includes: (a) blocking de novo synthesis of all cholesterol intermediates leading to an inability of Ras to stimulate cell growth and division, and (b) reducing the precursor supply for fatty acid synthase (FAS) and thus blocking tumor cell proliferation.

The present invention provides liposome delivery systems for the compositions of the present invention. Liposome formulations have the capacity to increase the solubility of hydrophobic drugs in aqueous solution. They often reduce the side effects associated with drug therapy. Liposomes are commonly prepared from naturally occurring phospholipids such as phosphatidylcholine, phosphatidylethanolamine, phosphatidylserine, phosphatidylglycerol, and phosphatidylinositol. Anionic phospholipids, such as phosphatidylglycerol, can be added to generate negative surface charge that provides for colloid stabilization. These phospholipids are often purified from natural sources, such as soybean and egg yolk, and also can be synthesized chemically with same or different fatty acids (saturated or unsaturated).

The nature and density of the surface charge of liposomes influence on stability, kinetics, biodistribution, and interaction with, and uptake by target cells. Liposome surface charge also influences the tendency for liposomes to aggregate, which makes liposome difficult to work with and affects uptake by target cells. Therefore, liposomes with a neutral surface charge have the highest tendency to aggregate, but are less likely to be cleared by cells of the reticuloendothelial system (RES) after systemic administration. On the other hand, negatively charged liposome exhibit reduced aggregation and increased stability and, therefore, exhibit non-specific cellular uptake in vivo. Thus, it has been suggested that a small amount of negatively charged lipids may stabilize neutral liposome against an aggregation-dependent uptake mechanism [Drummond et al., Pharm. Rev. 51, 691-743 (1999); D. C. Drummond, O. Meyer, K. Hong, D. B. Kirpotin, D. Papahadgopoulos, Pharm. Rev. 51, 691-743 (1999).] The negatively charged lipids may be natural or synthetically modified phospholipids. The present invention provides such methods and compositions for improved liposome formulation.

The present invention relates to the use of more defined pharmaceutically active guggulphospholipids and other bioactive molecules of present invention for treatment or prevention of abnormal cell growth, proliferation in inflammation, cholesterol lowering and weight loss, skin diseases such as acne affections, memory loss, and Alzheimer disease, neoplastic and cardiovascular diseases. Another object of the invention is the use of possible cationic or anionic or PEGylated analogues of pharmaceutically active novel compounds of present invention as drug carrier. Another object of this invention is the use of fatty acid-conjugated guggulsterones or guggulsterol in a composition with or without active agents or drugs and their uses in the treatment of human and animal diseases. Fatty acids may be short chain or long chain, saturated or unsaturated [e.g., guggulmyristate (C14:0); guggullinoleate (C18:3), etc.]. Additionally, the methods of the invention comprise administering a compound of invention as drug or in a pharmaceutical composition to combat mammalian diseases.

Synthetic guggulphospholipids of the present invention can conveniently be incorporated into liposomes, emulsion, micelles, vesicles, or complexes. Such liposome can also include one or more therapeutic agent. Such liposome and other formulations can be used to treat or alleviate cancer and other diseases, given orally in the form of liquid doses or inside enteric coated capsule or by i.v. injection. The formulation can be applied as liposome lip gels, ointment or cream for the treatment of skin diseases.

Another object of the present invention is to develop cognition enhancing effect of pharmaceutically active guggulphospholipids and other bioactive molecules of present invention given orally, topically, parenterally or by other method of administration in any pharmaceutical preparations and with amount necessary for activity.

Another object of the present invention is to develop a method of reducing, preventing or controlling hyperglycemic conditions by consuming pharmaceutically active guggulphospholipids and other bioactive products of the present invention in any pharmaceutically acceptable formulations. In addition, the guggulphospholipids can be consumed as a nutritional supplement for weight control, fat loss and hyperlipidemic properties. In any pharmaceutically acceptable formulations, the products of invention can be used with or without other excipients, as for example, high fiber, phosphate salts selected from the group consisting of calcium phosphate, potassium phosphate, sodium phosphate and the like, phospholipids (natural or synthetic) known in the art of liposome formulation. The phosphatidylcholine, preferably soy phosphatidylcholine or hydrogenated soy phosphatidylcholine will be used. Other phospholipids such as phosphatidylethanolamine, phosphatidylserine, phosphatidylinositol, phosphatidylglycerol, may also be used separately or mixture thereof. The phosphate salts are preferably a mixture of calcium, potassium and sodium salt. The weight control product may be administered in the form of capsule preferably enteric coated capsule, tablet, soft gel capsule, emulsion, syrup, food bar and the like.

In another embodiment of the invention, the pharmaceutically active products of the present invention is to use for the treatment of patients suffering from human memory dysfunction like Alzheimer's disease and Korasakoff's disease alone or in combination with other treatments. The compounds of the invention provide a new strategy in the treatment of neurodegenerative diseases, preferably Alzheimer's disease.

Another object of the present invention is to develop a method of improving conditions for the treatment of infected skin, for example some of the common fungal skin condition, and in general dermal dysfunctions.

Another object of the present invention is to develop a method of reducing, preventing or controlling HIV, abnormal cell growth, proliferation in inflammation, neoplasia and cardiovascular diseases by consuming novel products of the present invention in any pharmaceutically acceptable formulations.

One of the important objectives of the present invention is cancer prevention and treatment. Many animal studies have shown a definite positive correlation between dietary fat and the rate of tumor growth and the severity of metastases. It is well known that lipid synthesis in tumor cells is quite rapid. This phenomenon can be understood because rapidly dividing cells not only need fresh copies of DNA and proteins, but they also require the security of new biomembranes composed of phospholipids and cholesterol. The other major class of lipids, fatty acids, is also involved in tumor cell growth. Many human and experimental cancers express elevated levels of fatty acid synthase (FAS), the major enzyme required for endogenous fatty acid biosynthesis. The novel guggulphospholipid may induce programmed cell death in cancer cells.

An embodiment of the invention is the synthesis of compounds of present invention and their uses in liposomes, emulsion, micelles, vesicles and complexes. In the present invention, "biological activity" refers to cytotoxic, antiproliferative, and antioxidant activity against a cell, more preferably a cell associated with a disease condition. Preferably, the cell exhibits abnormal cell growth. A "disease" is referred to a neoplasia, a neurodegenerative disease, a pulmonary disease, an inflammatory disease, a cardiovascular disease, or skin disease. More preferably, a neoplasia is a solid tumor, leukemia or lymphoma. More preferably, a neurodegenerative disease is Alzheimer's disease. The individual compound or mixture of compounds of the present invention can be formulated into a pharmaceutical composition.

The invention may also regulate the synthesis of the vascular endothelial growth factor (VEGF). An embodiment of the invention is the stimulation of VEGF expression by the bioactive molecules of the present invention.

All products (e.g., compositions, complexes, etc.) of the present invention can be incorporated in common pharmaceutical compositions, such as are well known in the art.

DETAILED DESCRIPTION OF THE INVENTION

Figure 2:
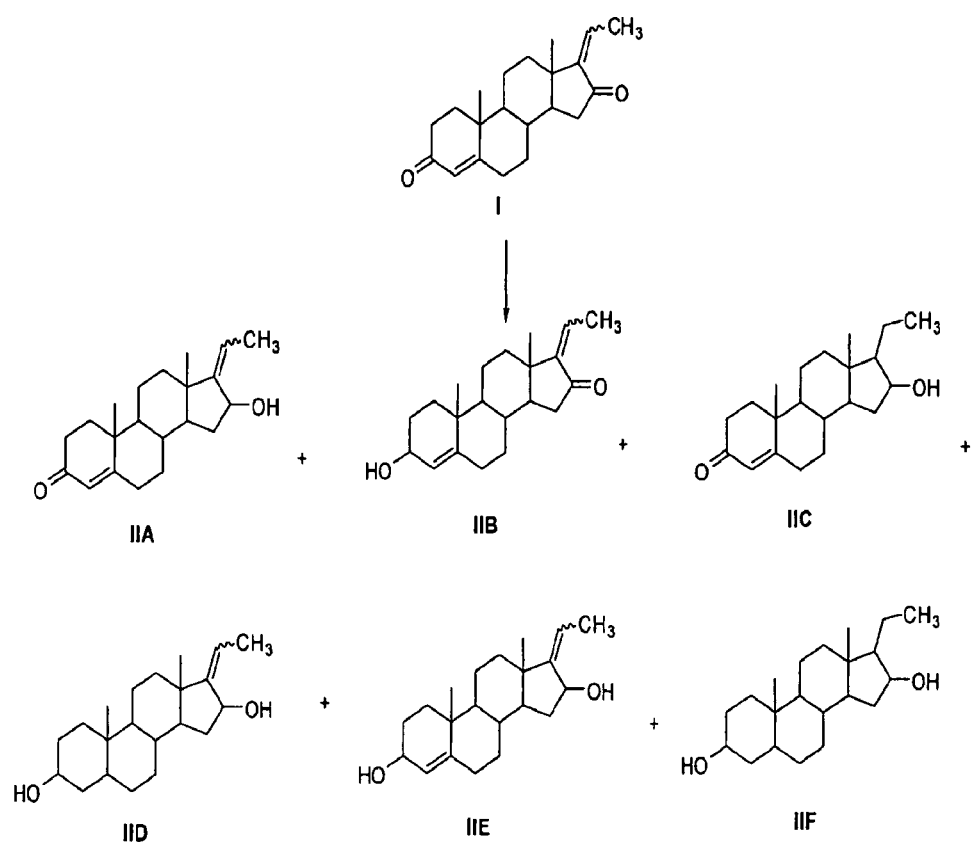

The present invention provides new and novel synthetic methods for producing and using pharmaceutically active guggulphospholipids, their fatty acid analogues and other bioactive molecules having the general formulas I, IIA, III-XI (FIGS. 1, 2). The compositions are useful for the prevention or treatment of conditions comprising but not limited to abnormal cell growth, proliferation in inflammation, cholesterol lowering and weight loss, skin diseases, memory loss, Alzheimer disease, neoplastic and cardiovascular diseases in humans and animals. This invention also provides their uses for preventing or controlling cognitive dysfunction, hyperglycemia, viral and skin infections. The present invention describes to the synthetic methods and uses of these pharmaceutically active molecules and compositions that contain them.

In Formulas III and IV, $R_1$ is a saturated or unsaturated acyl or alkyl groups having between 1 and 34 carbon atoms. In Formula V, at least one of $R_1$ or $R_2$ is preferably a saturated or unsaturated acyl group or alkyl group having between 1 and 34 carbon atoms. In a preferred embodiment, in Formulas V, $R_1$ and $R_2$ are the same and include from $C_1$ to $C_{34}$ saturated and/or unsaturated acyl or alkyl group, preferably between 6 and 24 carbon atoms and more preferably between 12 and 24 carbon atoms.

The term "alkyl" encompasses saturated or unsaturated straight chain and branched-chain hydrocarbon moieties. The term "substituted alkyl" comprises alkyl groups further bearing one or more substituents selected from hydroxyl, alkoxy (of a lower alkyl group), mercapto (of a lower alkyl group), cycloalkyl, substituted cycloalkyl, halogen, cyano, nitro, amino, amido, imino, thio, —C(O)H, acyl, oxyacyl (of a lower acyl) carboxyl and the like.

The term "acyl" encompasses saturated or unsaturated straight chain or branched fatty acid chain. The term "substituted acyl" comprises acyl groups further bearing one or more substituents selected from hydroxyl, alkoxy (of a lower alkyl group), mercapto (of a lower alkyl group), cycloalkyl, substituted cycloalkyl, halogen, cyano, nitro, amino, amido, imino, thio, —C(O)H, acyl, oxyacyl (of a lower acyl) carboxyl and the like. In formulas IV-X, X is hydrogen, methyl, ammonium, sodium, potassium, calcium, barium ion or any non-toxic ion, more preferably hydrogen, sodium or ammonium ion. In Formula VI, X and Y are same or different and are hydrogen, methyl, ammonium, sodium, potassium, calcium, barium ion or any non-toxic ion, more preferably hydrogen, sodium or ammonium ion.

In Formula IV, $R_1$ can also be sugar. Sugar is selected from a group consist of but not limited to allose, altrose, glucose, fructose, mannose, sucrose, galactose, sorbitol, glucosamine, glucuronic acid, talose, idose, gulose, ribose, deoxyribose, arabinose, xylose, and the like.

In Formula VIII, $R_3$, $R_4$ and $R_5$ are same or different and are H or methyl groups. Formula VIII is cationic guggul derivative, wherein X is a methyl group.

The PEG (polyethylene glycol) group in Formula X is a long chain, linear or branched synthetic polymer composed of ethylene oxide units, $HO(CH_2CH_2O)_nCH_2CH_2OCH_3$, in which n is typically between about 1 and about 1000 (such as between 1 and about 500) or otherwise can vary to provide compounds with molecular weights (M.W.) from 200-50,000 Daltons.

In Formula XI, a drug can be a therapeutically active agent linked directly or through a linker.

Formula XII is a cationic guggul derivative, wherein $R_6$, $R_7$, and $R_8$ are same or different and are hydrogen, methyl, alkyl, substituted alkyl, alkyoxy, substituted alkyloxy groups, optionally hydroxylated, aminated, or polyaminated having overall positive charge.

Guggul derivatives (III, XII), guggulphospholipids (III-X) and guggul-drug conjugates (XI) in the present invention can be in any form of geometric isomers. For example Formulas III-XII can be in the form of E-isomer or Z-isomer or mixture of E and Z isomers. Formulas III-XII in present invention can also be optically pure or mixture of optical isomers.

One embodiment of the present invention is set forth in FIG. 1, which shows novel approaches to the synthesis of guggul derivative (III, XII), guggulphospholipids IV-X, and guggul-drug conjugate (XI) starting from guggulsterol (IIA). Guggul derivative, guggulphospholipids and guggul-drug conjugate of Formulas III-XII can be prepared by any desired method, and the invention provides methods of preparing guggul derivatives, guggulphospholipids and analogues thereof. The method of preparing compounds III-XII from guggulsterol IIA in the present invention can be done in single step or a sequence of many steps.

In accordance with the inventive method, guggul derivatives of Formula III in the present invention can be prepared by the reaction of guggulsterol IIA with acyl chlorides in the presence of base in a suitable solvent. Specific examples of bases include but not limited to pyridine, triethylamine, diisopropylethylamine, diisopropylamine, butylamine and the like. Examples of suitable solvents include but not limited to, pyridine, triethylamine, dichloromethane, chloroform, tetrahydrofuran (THF), diethyl ether, t-butyl methyl ether, hexane, 1,2-dichloroethane, benzene, toluene, N,N-dimethylformamide (DMF) and the like.

Another method of the present invention involves methods of preparing guggul derivatives of formula III by the reaction of guggulsterol IIA with fatty acids and N,N'-dicyclohexyl carbodimide (DCC) or 1-ethyl-3-(3-dimethyl-aminopropyl)-carbodimide (EDC) in the presence of N,N'-dimethylaminopyridine (DMAP) in a suitable solvent. Examples of suitable solvents include but not limited to, dichloromethane, chloroform, tetrahydrofuran (THF), 1,2-dichloroethane, benzene, toluene, pyridine, N,N-dimethylformamide (DMF) and the like Another embodiment of the present invention involves methods of preparing Guggul phospholipids of Formula IV by reacting guggulsterol IIA with phosphoramidite reagent in an inert solvent (for example dichloroethane and the like) in presence of base (for example N,N-diisopropylethylamine or the like), then with alcohol (ROH) in presence of an activator such as 1H-tetrazole or the like followed by oxidation with tert-butylhydroperoxide or the like. The deprotection can be achieved by any suitable method, selected according to the protecting group present on the phosphate group. For example a methyl group can be removed with sodium iodide or trimethylamine, a benzyl group can be removed with sodium iodide or catalytic hydrogenolysis, cyanoethyl and fluoroenylmethyl groups by the treatment with a tertiary base such as triethylamine; a silyl group can be deprotected with fluoride ion or acidic medium.

Examples of suitable phosphoramidite reagents in the present invention include but are not limited to N, N-diisopropylmethylphosphoramidic chloride, (Bruzik et al, *Tet. Lett.* 1995, 36, 2415-2418;, (benzyloxy)(N, N-diisopropylamino)chlorophosphine (see, e.g., Prestwich et al. *J. Am. Chem. Soc.* 1991, 113, 1822-1825), benzyloxybis (diisopropylamino) phosphine (see, e.g., Dreef et al. *Tetrahedron Lett.* 1988, 29, 6513-6516), 2-cyanoethyl-N, N, N, N-tetraisopropylphosphoramidite (see, e.g., Browne et al. *J. Chem. Soc. Perkin Trans.* 1. 2000, 653-657.), (2-cyanoethyl)(N,N-diisopropylamino) diisopropylamino)chlorophosphine (see, e.g., Prestwich et al. *J. Org. Chem.* 1998, 63, 6511-6522; difluorenyl diisopropylphosphoramidite (see, e.g., Watanabe et al. *Tetrahedron Lett.* 1997, 38, 7407-7410) , methyl-N, N, N, N tetraisopropylphosphorodiamidite (see, e.g., Murakami et al. *J. Org. Chem.* 1999, 64, 648-651), dimethyl N, N-diisopropylphosphoramidite (see, e.g., Watanabe et al. *Tetrahedron Lett.* 1993, 34, 497-500), dibenzyl diisopropylphosphoramidite (see, e.g., Watanabe et al. *Tetrahedron Lett.* 2000, 41, 8509-8512), di-tert-butyl-N,N-diisopropylphosphoramidite (see, e.g., Lindberg et al. *J. Org. Chem.* 2002, 67, 194-199.), 2-(diphenylmethylsilyl)ethyl-N, N, N, N-tetraisopropylphosphoramidite (see, e.g., Chevallier et al. *Org. Lett.* 2000, 2, 1859-1861), (N-trifluoroacetylamino) butyl and (N-trifluoroacetylamino) pentyl-N, N, N, N-tetraisopropylphosphoramidites (see, e.g., wilk et al. *J. Org. Chem.* 1997, 62, 6712-6713). A preferred phosphoramidite reagent includes N, N-diisopropylmethylphosphoramidic chloride, and (2-cyanoethyl (N, N-diisopropylamino) chlorophosphine, and methyl-N, N, N, N tetraisopropylphosphorodiamidite.

Examples of other suitable phosphorylating reagents in the present invention include but are not limited to 2-bromoethyldichlorophosphate (Wissner, A. et al, *J. Med. Chem.* 1986, 29, 1315-1319), trimethylsilylethyl dicholorphosphate (Martin, S. F. et al, *J. Org. Chem.* 1994, 59, 4805-4820), methyl dichlorophosphate (Andresen, T. L et al, *J. Med. Chem.* 2005, 48, 7305-7314), 2-chloro-2-oxo-1,3,2-dioxaphospholane (Marx, M. H. et al, *J. Med. Chem.* 1988, 31, 858-863), 2-chloropheny dichlorophosphate phosphorus oxychloride (Andresen, T. L et al, *J. Med. Chem.* 2004, 47, 1694-1703).

Examples of suitable alcohols include but are not limited to alcohols of the formula ROH wherein R is a saturated or unsaturated acyl or alkyl group having between 1 and 34 carbon atoms. The terms "alkyl" encompasses saturated or unsaturated straight chain and branched-chain hydrocarbon moieties. The term "substituted alkyl" comprises alkyl groups further bearing one or more substituents selected from hydroxyl, alkoxy (of a lower alkyl group), mercapto (of a lower alkyl group), cycloalkyl, substituted cycloalkyl, halogen, cyano, nitro, amino, amido, imino, thio, —C(O)H, acyl, oxyacyl (of a lower acyl) carboxyl and the like.

Another embodiment of the present invention involves a method of preparation of guggulphospholipids of Formula V by reacting guggulsterol IIA with a phosphoramidite reagent in an inert solvent (for example, dichloromethane and the like) in presence of base (for example, N,N-diisopropylethylamine or the like), then with 1,2-disubstituted glycerol in presence of an activator such as, e.g., 1H-tetrazole or the like, followed by oxidation with tert-butylhydroperoxide or the like. The deprotection can be achieved by any suitable method, depending on the particular protecting group present on the phosphate group. Methods for deprotection are well known to those skilled in the art. For example, a methyl group can be removed with sodium iodide or trimethylamine, a benzyl group can be removed with sodium iodide or catalytic hydrogenolysis, cyanoethyl and fluoroenylmethyl groups by the treatment with a tertiary base such as triethylamine, and a silyl group can be deprotected with fluoride ion or acidic medium. Alternatively, 1,2-disubstituted glycerol can be first reacted with the phosphoramidite reagent and subsequently with guggulsterol IIA.

Another method in the present invention for the preparation of Formulas IV and V involves reaction of alcohol (ROH) or 1,2-disubstituted glycerol, respectively, with o-chlorophenyl dichlorophosphate (CPDCP) and, subsequently, with guggulsterol IIA in an inert solvent (for example, dichloromethane and the like) in the presence of base (for example, pyridine and the like) to provide the respective intermediates. The removal of o-chlorophenyl can be accomplished by reaction of respective intermediates with 2-pyridinealdoxime (PAO) and 1,1,3,3-tetramethylguanidine (TMG) to give IV and V respectively. Besides 2-pyridinealdoxime (PAO), other reagents such as 2-nitrobenzaldoxime in the presence of TMG can be used for the removal of o-chlorophenyl group.

Another method of the present invention for the preparation of Formulas IV and V involves reaction of alkyl phosphatidic acid or 1,2-disubstituted-sn-glycero-3-phosphatidic acid, respectively, with 1,2-dicyclohexylcarbodimide (DCC) and, subsequently, with guggulsterol IIA in an inert solvent (for example, dichloromethane and the like) in the presence of base (for example dimethylaminopyridine, DMAP) to provide IV and V respectively. Different salts of IV and V can be obtained by treating with appropriate bases. For example, treatment with dilute sodium hydroxide will provide sodium salt of IV and V, dilute potassium hydroxide will provide potassium salt of Formula IV and V, and dilute ammonium hydroxide will provide ammonium salt of Formula IV and V.

Yet another method of preparing guggulphosphate of Formula VI can be by reacting guggulsterol IIA with phosphorus oxychloride in presence of base (for example, pyridine and the like) in a suitable solvent (such as dichloromethane and the like) and later treating with water. Different salts of VI can be obtained by treating with appropriate bases. For example, treatment with dilute sodium hydroxide will provide sodium salt of VI, dilute potassium hydroxide will provide potassium salt of Formula VI, and dilute ammonium hydroxide will provide ammonium salt of Formula VI.

In another embodiment of the present invention, guggulsulfate of Formula VII is synthesized by reacting guggulsterol IIA with chlorosulfonic acid in presence of base (for example, pyridine and the like) in a suitable solvent (such as dichloromethane and the like). Different salts of VII can be obtained by treating with appropriate bases. For example, treatment with dilute sodium hydroxide will provide sodium salt of VII, dilute potassium hydroxide will provide potassium salt of Formula VII, and dilute solution of ammonium hydroxide will provide ammonium salt of formula VII.

In another embodiment of the present invention guggulphospholipid of Formula VIII ($R_3$, $R_4$, $R_5$=H) is prepared by the reaction of guggulsterol IIA with trimethylsilylethyl dicholorphosphate in presence of base (for example N,N-diisopropylethylamine or the like) in an inert solvent (for example tetrahydrofuran or the like) then with N-(tert-butoxycarbonyl)ethanolamine followed by oxidation with tert-butylhydroperoxide or the like. The deprotection of tert-butoxycarbonyl (Boc) group and trimethylsilylethyl group can be done under acidic condition (for example with trifluoroacetic acid and the like.

Yet another method for preparing Formula VIII ($R_3$, $R_4$, $R_5$=H) in the present invention involves reacting guggulsterol IIA with methyl dichlorophosphate in presence of base (for example triethylamine) in an inert solvent followed by reaction with N-(tert-butoxycarbonyl)ethanolamine. Deprotection of phosphate methyl group can be achieved with sodium iodide or trimethylamine.

Another embodiment of the present invention involves method of preparation of Formula VIII ($R_3$, $R_4$, $R_5$=$CH_3$) in the present invention can be synthesized by the reaction of guggulsterol IIA with 2-bromoethylchloro phosphate in presence of base (for example, triethylamine or pyridine and the like) followed by treatment with trimethylamine in suitable solvent such as chloroform and the like.

Another method of the preparation of Formula VIII ($R_3$, $R_4$, $R_5$=$CH_3$) involves reaction of guggulsterol IIA with 2-chloro-2-oxo-1,3,2-dioxaphospholane and subsequently reacting with trimethylamine in an inert solvent (for example, acetonitrile and the like).

Yet another method of preparing VIII ($R_3$, $R_4$, $R_5$=$CH_3$) involves reaction of guggulsterol IIA with phosphoramidite reagent in an inert solvent (for example dichloromethane and the like) in presence of base (for example N,N-diisopropylethylamine or the like), then with choline chloride in presence of an activator such as 1H-tetrazole or the like followed by oxidation with tert-butylhydroperoxide or the like. The deprotection can be achieved by any suitable method depending on the protecting group present on the phosphate group. For example a methyl group can be removed with sodium iodide or trimethylamine, a benzyl group can be removed with sodium iodide or catalytic hydrogenolysis, cyanoethyl and fluoroenylmethyl groups by the treatment with a tertiary base such as triethylamine; a silyl group can be deprotected with fluoride ion or acidic medium.

Formula VIII in the present invention can be obtained by another method of preparation in which guggulsterol IIA is reacted with phosphorus oxychloride in presence of base (for example, triethylamine and the like) and later with choline tosylate in suitable solvent such as pyridine and the like.

A method of preparing guggulphospholipids of Formula IX in the present invention involves reaction of guggulsterol with phosphoramidite reagent in the presence of base (for example, N,N-diisopropylethylamine and the like) in an inert solvent (for example, dichloromethane and the like) followed by reaction with 1,2-isopropylidene glycerol. The isopropylidene group can later be removed under acidic condition (such as HCl and the like) while the protecting groups on the phosphate can be achieved by any suitable method depending on the protecting group present on the phosphate group. For example a methyl group can be removed with sodium iodide or trimethylamine, a benzyl group can be removed with sodium iodide or catalytic hydrogenolysis, cyanoethyl and fluoroenylmethyl groups by the treatment with a tertiary base such as triethylamine; a silyl group can be deprotected with fluoride ion or acidic medium.

Formula X in the present invention is prepared by reacting guggulsterol IIA with methyl chlorophosphate in presence of base (for example triethylamine) in an inert solvent followed by reaction with N-(tert-butoxycarbonyl)ethanolamine to provide an intermediate which was subsequently reacted with mPEG-succinimidyl carbonate (SC-PEG). Deprotection of phosphate methyl group can be achieved with sodium iodide or trimethylamine.

Another embodiment of the present invention is to prepare guggul-drug conjugate having Formula XI as a prodrug by conjugating a drug with guggulsterol directly or through a linker Yet another embodiment of the present invention is to prepare cationic guggul derivatives (positively charged guggul derivatives) having formulas VIII (X=methyl group) and XII from guggulsterol IIA or guggulsterone I.

Guggulsterol in the present invention can be obtained commercially or synthesized as per the literature procedure. Guggulsterol in the present invention can be pure isomer or mixture of isomers. For example, guggulsterol can be Z-guggulsterol or E-guggulsterol or mixture of E-guggulsterol and Z-guggulsterol. Guggulsterols can be optically pure or mixture of optical isomers.

Another embodiment of the present invention, is represented in FIG. 2, in which guggulsterol is synthesized starting from guggulsterone I. Guggulsterone I on reduction with 9-borabicyclo[3.3.1]nonane (9-BBN) in suitable solvent (for example, methylene chloride, tetrahydrofuran or the like) will provide of IIA, IIB, or a mixture IIA and IIB. During reduction, it is conceivable that some quantities of Formulas IIC, IID, IIE and IIF will formed as minor products in addition to IIA and IIB during the reduction. Compound IIA can be isolated by column chromatography. Compound IIE on further oxidation with suitable oxidizing agent, for example, manganese dioxide (MnO2) in suitable solvent such as dichloromethane will provide compound IIA, IIB or mixture of IIA and IIB.

Another embodiment of the present invention, is represented in FIG. 2, in which guggulsterol is synthesized starting from guggulsterone I. Guggulsterone I on reduction with lithium aluminum hydride or sodium borohydride in suitable solvent (for example, methylene chloride, tetrahydrofuran or the like) will provide of IIA, IIB, or a mixture IIA and IIB. During reduction, it is conceivable that some quantities of Formulas IIC, IID, IIE and IIF will formed as minor product in addition to IIA and IIB during the reduction. Compound IIA can be isolated by column chromatography. Compound IIE on further oxidation with suitable oxidizing agent, for example, manganese dioxide (MnO2) in suitable solvent such as dichloromethane will provide compound IIA, IIB or mixture of IIA and IIB.

The term "prodrug" is defined as a pharmacologically inactive compound that is converted into an active agent by metabolic transformation. The objective is to chemically modify the drug (into its prodrug) in order to render it temporarily inactive. In vivo, via the action of enzyme(s), this prodrug then decomposes thereby liberating the active principle. In most cases, a judiciously selected chemical group is bound covalently to the active principle. This group will often govern the solubility of the prodrug, its stability, and the rate at which it liberates the active principle and the particular enzyme required for its transformation (Malet-Martino et al. *Curr. Med. Chem.-Anti-Cancer Agents,* 2002, 2, 267-310)

The term "linker" is defined herein as a group or chain containing one or more functional group for covalent binding with the lipid carrier and biologically active nucleoside. Preferred embodiments comprise a linker having at least two functional groups, wherein the linker has a first end and a second end and wherein the lipid is attached to the first end of the linker through a first linker functional group and the nucleoside is attached the second end of the linker through a second linker functional group. These groups can be designated either as weak or strong, based on the stability of the covalent bond which the linker functional group will form between the linker and either the lipid carrier or the biologically-active nucleoside. The weak functionalities include, but are not limited to, phosphoramidite, phosphoesters (such as phosphodiester, phosphotriester and phosphonate), carbonate, amide, carboxyl-phosphoryl anhydride, ester and thioester. The strong functionalities include, but are not limited to, ether, thioether, amine, amide, and ester. The use of a strong linker functional group between the linker and the nucleoside will tend to decrease the rate at which the compound will be released in vivo, whereas the use of a weak linker functional group between the linker and the nucleoside may act to facilitate in vivo release of the compound. In preferred embodiments, each of the first and second functional linker groups is a hydroxyl group, a primary or secondary amino group, phosphate group or substituted derivative thereof, a carboxylic acid, carbonate, carbamate or carbonyl group. The "linker" herein also comprises, in addition to the functional groups at either end, ($CH_2$) groups (where n=0-20) in the center optionally substituted with functional groups, such as alkyl, alkoxy, hydroxyl, carbonyl, carboxyl, carbamate, aldehyde, amino, halo, polyalkoxy, PEG groups, phosphate, phosphonate and pyrophosphate groups.

The inventive method can be used to prepare pharmaceutically active guggulphospholipids, their cationic and anionic analogues, their fatty acid analogues and variants comprising fatty acid/alkyl chain of varying length and saturation/unsaturation. The general structure of phospholipids comprises a fatty acid hydrocarbon chain and a carboxylic acid group. In general, the length of fatty acid hydrocarbon chain ranges from about 2 to about 34 carbons and can be saturated or unsaturated. However, the carbon chain is more typically between about 4 carbons and about 24 carbon atoms. In some embodiments, it is desirable for the hydrocarbon chain to comprise, for example, at least 6 carbon atoms or at least about 12 carbon atoms or at least about 14 carbon atoms. Typically, the length of fatty acid hydrocarbon is less than about 24 carbon atoms, or even less than about 20 carbon atoms. Indeed, an analogue of the present invention containing fatty acids/alkyl chains of intermediate length can also be prepared by the inventive method.

The term 'phosphate protecting group' used herein the invention refers to the commonly used protecting groups described by T. W. Greene and P. G. Wuts, *Protective Groups in Organic Synthesis,* 3 rd edition, John Wiley & Sons, New York (1999). Such protecting groups include alkyl phosphates including methyl, ethyl, cyclohexyl, t-butyl; 2-substituted ethyl phosphates including 2-cyanoethyl, 4-cyano-2-butenyl, 2-(methyldiphenylsilyl)ethyl, 2-(trimethylsilyl)ethyl, 2-(triphenylsilyl)ethyl; haloethyl phosphates including 2,2,2-trichloroethyl, 2,2,2-tribromoethyl, 2,2,2-trifluoroethyl; benzyl phosphates including 4-chlorobenzyl, fluorenyl-9-methyl, diphenylmethyl and amidates.

Phospholipids fatty acid typically are classified by the number of double or triple bonds in the hydrocarbon chain (unsaturation). A saturated fatty acid does not contain any double or triple bonds, and each carbon in the chain is bond to the maximum number of hydrogen atoms. The degree of unsaturation of fatty acid depends on the number of double or triple bonds in the hydrocarbon chain. In this respect, a monounsaturated fatty acid contains one double bond, whereas a polyunsaturated fatty acid contains two or more double bonds [e.g., Oxford *Dictionary of Biochemistry and Molecular Biology*, rev. ed., A. D. Smith (ed.), Oxford University Press (2000), and Molecular Biology Of the Cell, 3rd ed., B. A. Alberts (ed), Garland Publishing, New York (1994)]. Fatty acids of varying chain length and unsaturation can be used to prepare compounds of present invention. Preferred fatty acids range from carbon chain length of about 2 to 34, preferably between about 4 and about 24 carbons or even less than about 20 carbon atoms, and include tetranoic acid(C4:0), pentanoic acid(C5:0), hexanoic acid (C6:0), heptanoic acid(C7:0), octanoic acid(C8:0), nonanoic acid(C9:0), decanoic acid (C10:0), undecanoic acid(C11:0), dodecanoic acid(C12:0), tridecanoic acid(C13:0), tetradecanoic(myristic) acid(C14:0), pentadecanoic acid (C15:0), hexadecanoic (palmatic) acid (C16:0), heptadecanoic acid(C17:0), octadecanoic(stearic)acid(C18:0), nonadecanoic acid(C19:0), eicosanoic(arachidic)acid(C20:0), heneicosanoic acid(C21:0), docosanoic (behinic)acid (C22:0), tricosanoic acid(C23:0), tetracosanoic acid(C24:0), 10-undecanoic acid (C11:1), 11-dodecanoic acid(C12:1), 12-tridecanoic acid(C13:1), myristoleic acid (C14:1), 10-pentadecaenoic acid(C15:1), palmitoleic acid(C16:1), oleic acid(C18:1), linoleic acid(C18:2), linolenic acid(C18:3), eicosenoic acid(C21:1), eicosadienoic acid(C20:2), eicosatrienoic acid (C20:3), arachidonic acid(cis-5,8,11,14-eicostetraenoic acid), and cis-5,8,11,14,17-eicospentaenoic acid. Other named fatty acids can also be used. Examples of such include saturated fatty acids such as ethanoic(or acetic) acid, propanoic(or propionic)acid, butanoic(or butyric)acid, hexacosanoic(or cerotic)acid, octacosanoic(or montanic) acid, tricontanoic(or melissic)acid, dotricontanoic(or lacceroic) acid, tetratricontanoic(or gheddic)acid, pentatricontanoic(or ceroplastic)acid, and the like; mono-unsaturated fatty acids such as trans-2-butenoic(or crotonic)acid, cis-2-butenoic(or isocrotonoic)acid, 2-hexenoic(or isohydrosorbic)acid, 4-decanoic(or obtusilic)acid, 9-decanoic(or caproleic)acid, 4-dodecenoic(or linderic)acid, 5-dodecenoic (or denticetic) acid, 9-dodecenoic(lauroleic)acid, 4-tetradecenoic(or tsuzuic)acid, 5-tetradecenoic(or physeteric)acid, 6-octadecenoic(or petroselenic)acid, trans-9-octadecenoic (or elaidic)acid, trans-1'-octadecenoic(or vaccinic)acid, 9-eicosenoic(or gadoleic)acid, 1'-docosenoic(or cetoleic) acid, 13-decosenoic(or erucic)acid, 15-tetracosenoic(or nervonic)acid, 17-hexacosenoic(or ximenic)acid, 21-triacontenoic(or lumequeic)acid, and the like; dienoic unsaturated fatty acids such as 2,4-pentadienoic(or β-vinylacrylic)acid, 2,4-hexadienoic(or sorbic)acid, 2,4-decadienoic(or stillingic)acid; 2,4-dodecadienoic acid; 9,12-hexadecadienoic acid; cis-9-cis-12-octadecadienoic(or α-linoleic)acid; trans-10-trans-12-octadecadienoic(or linoleaidic)acid; trans-11-trans-12-octadecadienoic acid; 11,14-eicosadienoic acid; 13,16-docosadienoic acid; 17,20-Hexacosadienoic acid and the like; trienoic unsaturated fatty acids such as 6,10,14-hexadecatrienoic (or hiragonic) acid; 7,10,13-hexadecatrienoic acid; cis-6-cis-9-cis-12-Octadecatrienoic (or γ-linoleic) acid; trans8-trans-10-trans-12-octadecatrienoic (or β-calendic) acid; cis-8-trans-10-trans-12-octadecatrienoic (or β-calendic) acid; cis-8-trans-10-cis-12-octadecatrienoic acid; cis-9-cis-12-cis-15-octadecatrienoic(or α-linolenic) acid; trans-9-trans-12-trans-15-octadecatrienoic(or α-linolenelaidic)acid; cis-9-trans-1'-trans-13-octadecatrienoic(or α-eleostearic)acid; trans-9-trans-1'-trans-13-octadecatrienoic(or β-eleostearic)acid; cis-9-trans-11-cis-13-octadecatrienoic(or punicic) acid; 5,8,11-eicosatrienoic acid; 8,11,14-eicosatrienoic acid and the like; tetraenoic unsaturated fatty acids such as 4,8,11,14-hexadecatetraenoic acid; 6,9,12,15-hexadecatetraenoic acid; 4,8,12,15-octadecatetraenoic(or moroctic)acid; 6,9,12,15-octadecatetraenoic acid; 9,11,13,15-octadecatetraenoic(or α- or β-parinaric)acid; 9,12,15,18-octadecatetraenoic acid; 4,8,12,16-eicosatetraenoic acid; 6,10,14,18-eicosatetraenoic acid; 4,7,10,13-docastetraenoic acid; 7,10,13,16-docosatetraenoic acid; 8,12,16,19-docosatetraenoic acid and the like; penta- and hexaenoic unsaturated fatty acids such as 4,8,12,15,18-eicospentaenoic(or timnodonic)acid; 4,7,10,13,16-docospentaenoic acid; 4,8,12,15,19-docospentaenoic(or clupanodonic)acid; 7,10,13,16,19-docosapentaenoic acid; 4,7,10,13,16,19-docosahexaenoic acid; 4,8,12,15,18,21-tetracosahexaenoic(or nisinic)acid and the like; branched chain fatty acids such as 3-methylbutanoic(or isovaleric) acid; 8-methyldodecanoic acid; 10-methylundecanoic(or isolauric)acid; 11-methyldodecanoic(or isoundecylic)acid; 12-methyltridecanoic (orisomyristic)acid; 13-methyltetradecanoic(or isopentadecylic)acid; 14-methylpenta-decanoic (or isopalmitic)acid; 15-methylhexadecanoic acid; 10-methylheptadecanoic acid; 16-methylheptadecanoic(or isostearic)acid; 18-methylnonadecanoic(or isoarachidic)acid; 20-methylheneeicosanoic(or isobehenic)acid; 22-methyltricosanoic(or isolignoceric)acid; 24-methylpentacosanoic(or isocerotic)acid; 26-methylheptacosanoic(or isomonatonic) acid; 2,4,6-trimethyloctacosanoic(or mycoceranic or mycoserosic)acid; 2-methyl-cis-2-butenoic(angelic)acids; 2-methyl-trans-2-butenoic(or tigilic)acid; 4-methyl-3-pentenoic(or pyroterebic)acid, and the like.

Guggulphospholipids of the present invention can conveniently be incorporated into liposomes, emulsion, micelles, vesicles or complexes. Such liposome can also include one or more therapeutic agent. Such formulations according to the present invention can be prepared by any suitable technique. The invention provides a method for preparing a liposome, emulsion, micelles, vesicles, complexes or other lipid formulation comprising a novel guggulphospholipid or other bioactive molecules of the present invention.

The liposome composition or complexes including micelles, vesicles, and emulsions can also include other lipids, for example, the composition can include one or more natural or synthetic phospholipid. The phospholipids will be selected from the group consisting of phosphatidylcholine, soy phosphatidylcholine, hydrogenated soy phosphatidylcholine and mixture thereof, egg phosphatidylcholine, dilauryloylphosphatidylcholine, dimyristoylphosphatidylcholine, dipalmitoylphosphatidylcholine, disteroylphosphatidylcholine, dioleylphosphatidylcholine, dielaidoylphosphatidylcholine, diarachidonoylphosphatidylcholine and mixture thereof in different molar ratio, phosphatidylethanolamine, sphingomyelin, dimyristoyl phosphatidylethanolamine, dipalmitoyl phosphatidylethanolamine, brainsphingomyelin, dipalmitoyl sphingomyelin, disteroyl sphingomyelin and mixtures thereof. The novel guggulphospholipid of the present invention comprises guggulsterones or guggulsterol, which can serve as substitute of cholesterol or derivatives of cholesterol. Alternatively or additionally, the composition can include one or more sterols if necessary such as, cholesterol, derivatives of cholesterol, cholesteryl esters, coprostanol, cholestanol, cholestane, cholesterol hemisuccinate, cholesterol sulfate, guggulsterols, and derivatives of guggulsterols, guggulsulfate, guggulsteryl esters, and mixtures thereof.

The liposome composition or complexes including micelles, vesicles and emulsions can also include one or more negatively charged phospholipids. The negatively charged phospholipids will be selected from the group consisting of phosphatidylglycerol, phosphatidylserine, phosphatidic acid, poly(ethylene glycol)-phosphatidylethanolamine, dilauroylphosphatidyl glycerol, dimyristoylphosphatidyl glycerol, dipalmitoylphosphatidyl glycerol, distearoylphosphatidyl glycerol, dioleoylphosphatidyl glycerol, dimyristoyl phosphatidic acid, dipalmitoyl phosphatidic acid, dimyristoyl phosphatidyl serine, dipalmitoyl phosphatidyl serine, brain phosphatidyl serine, and mixtures thereof.

The liposome composition or complexes including micelles, vesicles and emulsions can also include one or more positive charge lipids. Examples of positive charge lipids in the present invention include compounds of formula XII and VIII (where X is a methyl group). The liposome or complexes may further contain phospholipids such as phosphatidylcholine, phosphatidylglycerol and cholesterol or cholesterol derivative in certain ratio such that the said liposome or complexes have a net overall positive charge.

The liposome composition or complexes including micelles, vesicles and emulsions can also include stabilizers, absorption enhancers, antioxidants, biodegradable polymers and medicinally active agents among other ingredients. In some embodiments, it is preferable for the inventive composition, especially liposome composition, to include one or more targeting agents, such as carbohydrate or protein or other ligand that binds to a specific substrate, for example, that recognize cellular receptors. The inclusion of such agents, such as carbohydrate or one or more proteins selected from groups of proteins consisting of antibodies, antibody fragments, peptides, peptide hormones, receptor ligands such as an antibody to a cellular receptor and mixtures thereof, can facilitate targeting a liposome to a predetermined tissue or cell type.

The liposome composition or complexes including micelles, vesicles and emulsions can also include one or more active agents for the medicinal use. A single active agent can be included, or a mixture of active agents (e.g., two or more active agents) can be included within the composition. Active agents (or "drugs") can be present in any suitable manner in the composition. For example, they can be complexes with the pharmaceutically active guggul-phospholipids of the present invention and their analogues in the composition. Additionally, or alternatively, one or more active agents can be entrapped within liposome, when the composition is a liposome composition.

Drugs, active agents or therapeutic agents that are compatible with the present invention include, for example, agents which act on the peripheral nerves, adrenergic receptors, cholinergic receptors, the skeletal muscles, the cardiovascular system, smooth muscles, the blood circulatory system, synaptic sites, neuroeffector functional sites, endocrine and hormone systems, the immunological system, the reproductive system, the skeletal system, the alimentary and excretory systems, the histamine system and the central nervous system. Suitable agents may be selected from, for example, proteins, enzymes, and hormones, nucleotides (including sense and antisense oligonucleotides) (e.g., U.S. Pat. No. 6,126,965, 2000), polynucleotide, nucleoproteins, polysaccharides, glycoproteins, lipoproteins, polypeptides, steroids. Active agents can be analgesics, anesthetics, antiarrhythmic agents, antibiotics, antiallergic agents, antifungal agents, anticancer agents, anticoagulants, antidepressants, antidiabetic agents, anti-epilepsy agents, anti-inflammatory corticosteroids, agents for treating Alzheimer's or Parkinson's disease, antiulcer agents, anti-protozoal agents, anxiolytics, thyroids, anti-thyroids, antiviral, anorectics, bisphosphonates, cardiac inotropic agents, cardiovascular agents, corticosteroids, diuretics, dopaminergic agents, gastrointestinal agents, hemostatics, hyper cholesterol agents, antihypertensive agents (e.g., dihydropyridines), antidepressants, and cox-2 inhibitors, immunosuppressive agents, anti-gout agents, anti-malarials, steroids, terpinoids, triterpines, retinoid, anti-ulcer H2-receptor antagonists, hypoglycemic agents, moisturizers, cosmetics, anti-migraine agents, anti-muscarinic agents, anti-inflammatory agents, such as agents for treating rheumatology, arthritis, psoriasis, inflammatory bowel disease, Crohn's disease, or agents for treating demyelinating diseases including multiple sclerosis, ophthalmic agents, vaccines (e.g., against pneumonia, hepatitis A, hepatitis B, hepatitis C, cholera toxin B subunit, influenza virus, typhoid, plasmodium falciparun, diphtheria, tetanus, HSV, tuberculosis, HIV, SARS virus, perpetual pertussis, measueles, mumps and rubella vaccine (MMV), bacterial toxins, vaccinea virus, adenovirus, canary, polio virus, bacillus calmette guerin (BCG), klebsiella pneumonia, etc.), histamine receptor antagonists, hypnotics, kidney protective agents, lipid regulating agents, muscle relaxants, neuroleptics, neurotropic agents, opioid agonists and antagonists, parasympathomimetics, protease inhibitors, prostaglandins, sedatives, sex hormones (e.g., estrogen, androgen), stimulants, sympathomimetics, vasodilators and xanthenes and synthetic analogs of these species. The therapeutic agents can be nephrotoxic, such as cyclosporine and amphotericin B, or cardiotoxic, such as amphotericin B and paclitaxel. Exemplary anticancer agents include melphalan, chlormethine, extramustinephosphate, uramustine, ifosfamide, mannomustine, trifosfamide, streptozotocin, mitobronitol, mitoxantrone (see., e.g., international patent application WO 02/32400), methotrexate, fluorouracil, cytarabine, tegafur, idoxide, taxanes [(e.g., taxol, paclitaxel, etc., see international patent application WO 00/01366; U.S.Pat. No. 5,415,869)], daunomycin, daunorubicin, bleomycin, etoposide, tamoxifen, hydroxytamoxifen, endoxifen carboplatin, cis-platin, paclitaxel, BCNU, vinca alkaloids (e.g., vincristine, vinorelbine (e.g., international patent application WO 03/018018, and the like) camptothecin and derivatives thereof (e.g., international patent application WO 02/058622), SN 38, irinotecan (e.g., international patent application WO 03/030864, and the like), cytokines, ribozymes, interferon's,oligonucleotides and functional anthracyclines, antibodies, cytoxines, doxorubicin, etopside, derivatives of the foregoing. Additional examples of drugs which may be delivered according to the method include, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridi-hexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetra nitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyl testosterone, 17- β-estradiol, ethinyl estradiol, ethinyl estradiol 3-methyl ether, prednisolone, 17- α-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenyl-alanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, colchicine, glucagon, thyroid stimulating hormone, parathyroid and pituitary hormones, digestive hormones, calcitonin, rennin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferon's (e.g., consensus interferon, interferon α-2α, interferon α-2β, α-, β-, or γ- interferon's), interleukins, growth hormones such as human growth hormone and its derivatives such as methione-human growth hormone and desphenylalanine human growth hormone, bovine growth hormone and porcine growth hormone, fertility inhibitors such as the prostaglandins, fertility promoters, growth factors such as insulin-like growth factor, coagulation factors, pancreas hormone releasing factor, analogues and derivatives of these compounds, and pharmaceutically acceptable salts of these compounds, or their analogues or derivatives. The therapeutic agent can be a mixture of drugs or agents (e.g., two or more agents) that can be beneficially co administered in the liposome formulation. The methods and compositions of the present invention find use with the methods and compositions disclosed in U.S. application Ser. No. 60/850,446, file Oct. 10, 2006, which is incorporated by reference herein in its entirety.

Generally, liposome or complexes including micelles, vesicles and emulsions can have a net neutral, negative or positive charge. For example, positive liposome can be formed from a solution containing natural or synthetic phosphatidylcholine, cationic phosphatidylcholine of the present invention with or without cholesterol and enough stearylamine to overcome the negative charge if any. Negative liposome can be formed from solutions containing natural or synthetic phosphatidylcholine, cholesterol, and phosphatidylglycerol or negatively charged phosphatidylcholine variants prepared by the methods described herein.

The liposome or complexes including micelles, vesicles and emulsions of the present invention can be multi or unilamellar vesicles depending on the particular composition and procedure to make them. Liposome or complexes including micelles, vesicles and emulsions can be prepared to have substantially homogeneous sizes in a selected size range, such as about 20 micron or less, or about 10 micron or less, or about 5 micron or less, or about 1 micron or less, or about 500 nm or less, about 200 nm or less, or about 100 nm or less. One effective sizing method involves extruding an aqueous suspension of the liposome through a series of polycarbonate membranes having a selected uniform pore size; the pore size of the membrane will correspond roughly with the largest sizes of liposome produced by extrusion through that membrane.

The liposome composition or complexes including micelles, vesicles and emulsions can be in any desired form. For example, for pharmaceutical use, the composition can be ready for administration to a patient. Alternatively, the composition can be in dried or lyophilized form. Where the composition is dried or lyophilized, preferably the composition includes a cryoprotectant as well. Suitable cryoprotectants include, for example, sugars such as trehalose, maltose, lactose, sucrose, glucose, and dextran, with the most preferred sugars from a performance point of view being trehalose and sucrose. Other more complicated sugars can also be used, such as, for example, amino glycosides, including streptomycin and dihydrostreptomycin.

Any suitable method can be employed to form the liposome or complexes including micelles, vesicles and emulsions. For example, lipophilic liposome-forming or lipophilic complex-forming ingredients, such as natural or synthetic phosphatidylcholine, pharmaceutically active guggulphospholipids of the present invention, with or without cholesterol or cholesterol derivatives, and α-tocopherol can be dissolved or dispersed in a suitable solvent or combination of solvents and dried. Suitable solvents include any ionic solvent or any non-polar or slightly polar solvent, such as t-butanol, ethanol, methanol, chloroform, or acetone that can be evaporated without leaving a pharmaceutically unacceptable residue. Drying can be by any suitable means such as by lyophilization. The dehydration is typically achieved under vacuum and can take place either with or without prior freezing of the liposome preparation. Hydrophilic ingredients can be dissolved in polar solvents, including water.

Mixing the dried lipophilic ingredients with the hydrophilic mixture can form liposome or complexes. Mixing the polar solution with the dry lipid film can be by any means that strongly homogenizes the mixture. Vortexing, magnetic stirring and/or sonicating can effect the homogenization.

Where active agents (or a mixture of active agents) are included in the liposome or complexes, the invention provides a method for retaining a drug in a liposome or complexes. The pharmaceutically active guggulphospholipids of the present invention, their analogues or other bioactive molecules as described herein and a drug or drugs (e.g., an active agent or a mixture of active agents) is included within a liposome or a complex. For example, active agent(s) can be dissolved or dispersed in a suitable solvent and added to the liposome mixture prior to mixing. Typically hydrophilic active agents will be added directly to the polar solvent and hydrophobic active agents will be added to the non polar solvent used to dissolve the other ingredients but this is not required. The active agent could be dissolved in a third solvent (e.g., ionic solvent or solvent mix and added to the mixture of polar solvent with the lipid film prior to homogenizing the mixture.

Liposome or complexes including micelles, vesicles and emulsions can be coated with biodegradable polymers such as sucrose, epichlorohydrin, branched hydrophilic polymers of sucrose, polyethylene glycols, polyvinyl alcohols, methoxypolyethylene glycol, ethoxypolyethylene glycol, polyethylene oxide, polyoxyethylene, polyoxypropylene, cellulose acetate, sodium alginate, N,N-diethylaminoacetate, block copolymers of polyoxyethylene and polyoxypropylene, polyvinyl pyrrolidone, polyoxyethylene X-lauryl ether wherein X is from 9 to 20, and polyoxyethylene sorbitan esters.

Antioxidants can be included in the liposome composition, complexes or other lipid composition. Suitable antioxidants include compounds such as ascorbic acid, tocopherol, and deteroxime mesylate.

Absorption enhancers can be included in the liposome composition, complexes or other lipid composition. Suitable absorption enhancers include sodium salicylate-chenodeoxycholate, sodium deoxycholate, polyoxyethylene 9-lauryl ether, chenodeoxy cholate-deoxycholate and polyoxyethylene 9-lauryl ether, monoolein, sodium tauro-24,25-dihydrofusidate, sodium taurodeoxycholate, sodium glycochenodeoxycholate, oleic acid, linoleic acid, linolenic acid. Polymeric absorption enhancers can also be included such as polyoxyethylene ethers, polyoxyethylene Sorbian esters, polyoxyethylene 10-lauryl ether, polyoxyethylene 16-lauryl ether, azone (1-dodecylazacycloheptane-2-one).

The inventive lipid (and their liposome or complexes) composition also can include one or more pharmaceutically acceptable excipients. For example, pharmaceutically suitable excipients include solid, semi-solid or liquid diluents, fillers and formulation auxiliaries of all kinds. The invention also includes pharmaceutical preparations in dosage units. This means that the preparations are in the form of individual parts, for example vials, syringes, capsules, pills, suppositories, or ampoules, of which the content of the liposome or complex formulation of active agent corresponds to a fraction or a multiple of an individual dose. The dosage units can contain, for example, 1, 2, 3, or 4 individual doses, or ½, ⅓, or ¼ of an individual dose. An individual dose preferably contains the amount of active agent which is given in one administration and which usually corresponds to a whole, a half, a third, or a quarter of a daily dose.

Tablets, dragees, capsules, preferably enteric coated capsules or tablets, pills, granules, suppositories, solutions, suspensions, emulsions, pastes, ointments, gels, creams, lotions, powders and sprays can be suitable pharmaceutical preparations. Suppositories can contain, in addition to the liposome active agent, suitable water-soluble or water-insoluble excipients. Suitable excipients are those in which the inventive liposome active agent is sufficiently stable to allow for therapeutic use, for example polyethylene glycols, certain fats, and esters or mixtures of these substances. Ointments, pastes, cream, and gels can also contain suitable excipients in which the liposome active agent is stable. The composition also can be formulated for injection (e.g., intravenously, interstitially, intratumorally, etc) by the inclusion of one or more excipients (e.g., buffered saline) suitable for injection.

The active agent or its pharmaceutical preparations can be administered intravenously, subcutaneously, locally, orally (as emulsion or liquid or capsule), parenterally, intraperitoneally and/or rectally or by direct injection into tumors or sites in need of treatment by such methods as are known or developed. Pharmaceutically active guggulphospholipids and their analogues and other bioactive molecules of the present invention can be administered topically, e.g., as a cream, skin ointment, dry skin softener, moisturizer, etc Where the composition includes one or more active agents (e.g., a mixture of active agents), the invention provides for the use of the composition to prepare a medicament for the treatment of a disease. In this sense, the invention also provides a method for treating a human or animal disease. In accordance with the inventive method, the inventive composition containing one or a mixture of active agents is exposed to (administered to) a human or animal patient in need of such treatment. In this manner, the active agent(s) are delivered to the patient. The preferred animal in the present invention is a mammal.

The method can be used to administer one or more active agents. It is thought to be general for active agents that are stable in the presence of surfactants. Hydrophilic active agents are suitable and can be included in the interior of the liposome such that the liposome bilayer creates a diffusion barrier preventing it from randomly diffusing throughout the body. Hydrophobic active agents are thought to be particularly well suited for use in the present method because they not only benefit by exhibiting reduced toxicity but they tend to be well solubilized in the lipid bilayer of liposome.

In certain embodiments wherein the active agent is polynucleotide, the methods of the present invention find application in the transfection of a cell or cells with the polynucleotide. The methods of the embodiment can be employed to transfect cells in vitro, or to deliver therapeutic or diagnostic polynucleotides to cells in vivo. For example, methods of these embodiments can be used to deliver genes to cells in culture or to patients in connection with gene therapy regimens. For therapeutic applications, such embodiments of the invention thus provide methods of gene therapy comprising, e.g., administering a pharmaceutical composition comprising one or more nucleic acids to a patient in need of treatment, wherein the composition comprises cationic lipid (for example, formula XII). In some embodiments, the polynucleotide comprises an expression construct encoding a gene, such that the gene is expressed within the cell after transfection in accordance with the inventive method.

A lipid composition of the present invention can be used to facilitate the intercellular delivery of oligonucleotides such as DNA, mRNA, antisense oligonucleotides or siRNA, and sequences coding for therapeutically active polypeptides. Thus catonic lipid-mediated delivery of DNA, mRNA, antisense oligonucleotides, siRNA or proteins in accordance with embodiments of the invention can provide therapy for various diseases, including but not limited to genetic diseases.

In some embodiments, the invention also provides a kit for transfection of polynucleotides into cells. The kit includes, e.g., cationic lipid (for example, Compound XII) and can also include (but need not include) a desired polynucleotide for transfection. The kit can also include the reagents for facilitating transfection, such as buffers, culture medium, etc.

Examples of therapeutic polynucleotides include antisense oligonucleotides such as antisense RNA or DNA sequences, small interfering RNA (siRNA), microRNA (miRNA), ribozymes, and aptamers. In some embodiments, therapeutic polynucleotides target desired nucleic acid or amino acid sequences within cells, such as genes or gene products associated with a disease state (e.g., oncogenes or viral genes). A preferred therapeutic polynucleotide for targeting desired genes is a 10 to 40-mer antisense polynucleotide or 10-40-mer siRNA sequences, preferably between 15 to 25-mer sequences. Where oligonucleotides are included in the composition, they may contain one or more modifications, e.g., phosphothioate linkages or 2' O-methyl ribose, e.g. to alter characteristics such as nuclease resistance, hybridization behavior, etc. In some preferred embodiments, a polynucleotide of the present invention comprises two phosphothioate linkages. In certain embodiments comprising two phosphothioate linkages, a polynucleotide composition of the present invention may contain one phosphothioate linkage at each terminal end, however the linkages can be present anywhere from one end to the other end (e.g. in between the ends) of an oligonucleotide. A polynucleotide can be single-stranded or double-stranded.

Diseases in which the compositions of the present invention find use for treatment will depend on the selection of active agents, such as described herein. In preferred embodiments, at least one active agent incorporated into the composition is an anticancer agent (e.g., a chemotherapeutic agent) for use in treating cancer. Chemotherapeutic agents are well suited for such use. Liposome formulations or complexes including micelles, vesicles and emulsion containing chemotherapeutic agents may be injected directly into the tumor tissue for delivery of the chemotherapeutic agent directly to cancer cells. In some embodiments, e.g., after resection of a tumor, the liposome formulation can be implanted directly into the resulting cavity, and/or may be applied to the remaining tissue as a coating. In cases in which the liposome formulation or complex is administered after surgery, it is possible to utilize liposome having larger diameters of about 1 micron since they do not have to pass through the vasculature. Compositions according to the present invention find use in any type of cancer, and particularly in cancer in a mammal. Examples include, but are not limited to, cancers of the head, neck, brain, blood, (e.g., leukemia, acute leukemia, acute lymphocytic leukemia, acute myelocytic leukemia, lymphoma, myeloma), breast, lung, pancreas, bone, spleen, bladder, prostate, testes, colon, kidney, ovary and skin (e.g. Kaposi's sarcoma), bone marrow, liver, stomach, tongue, mouth and larynx. Active compound-lipid complexes of the present invention also find use in reducing the tendency of cancer cells to develop a resistance to other therapeutic agents such as anti-cancer agents, chemotherapy and radiation. Thus, other therapeutic agents can be advantageously employed with the present invention in the formation of an active combination or by separate administration (e.g., other therapeutic agents may be used before, after, or administered at the same time as the compositions of the invention).

The compositions of the present invention can be employed to treat infections caused by numerous fungi and parasites, including but not limited to, *Acremonium* sp., *Aspergillus fumigatus*, *Aspergillus pneumonia*, *Blastomyces dermatitidis*, *Candida albicans*, *Candida guillermondi*, *Candida tropicalis*, *Coccidioides immitis*, *Cryptococcus neoformans*, *Fusarium* sp., *Histoplasma capsulatum*, *Mucor mucedo*, *Rhodotorula* sp., *Sporothrix schenckii*, *Acanthamoeba polyphaga*, *Entomophthora* sp., *Histoplasma capsulatumm Leishmania brasiliensis*, *Rhizopus* sp., *Rhodotorula* sp., *Torulopsis glabrata*, *Paracoccidioides brasiliensis*. Additional fungal pathogens include *Trichosporon*, *Muco*, *Alternaria*, *Bipolaris*, *Curvularia*, etc The compositions of present invention also find use in the treatment of Visceral Leishmaniasis also called as Kala-azar and infections caused by *Leishmania donovani* complex, *L.d donovani*, *L.d infantum*, *L.d archibaldi*, *L.d chagasi*, *Phlebotomus* sp. and *Lutzomya logipalpis*.

The compositions of present invention can also be employed to treat viral infections, such as those caused, e.g., by human immunodeficiency virus (HIV), herpes simplex viruses (HSV-1 and HSV2), hepatitis C virus (HCV), human papilloma virus (HPV) and cyotomegalovirus (CMV).

In some embodiments, the inventive active compound-lipidcomplex (for example, a tacrolimus-lipid complex) is employed to treat rejection reactions caused by organ transplantations and can be administered organ or tissue transplantation, e.g., in a mammal. In this regard, the invention provides a methods and compositions for preventing organ or tissue rejection comprising administering to a subject (e.g. a patient having an organ or tissue transplantation) a composition comprising a complex of active compound lipid-complex and lipid(s) in an amount sufficient to prevent an organ or tissue rejection within the subject.

Yet other diseases for treatment using liposome formulations or complexes of the invention include (but are not limited to) prevention or treatment of abnormal cell growth, proliferation in inflammation, cholesterol lowering and weight loss, skin diseases, memory loss, Alzheimer disease, neoplastic and cardiovascular diseases, anti-hyperglycemic, cognition enhancer, skin ointment, and HIV.

Embodiments of the invention also are directed to methods of delivering pharmaceutically active guggulphospholipids and their analogues as active agents (or in combination with or without other active agents as mixture) to cells. The methods can be carried out by preparing liposome or complexes including micelles, vesicles and emulsion that include active agents and pharmaceutically active guggulphospholipids, their analogues and/or other bioactive molecules of the present invention. The liposome or complex is then delivered to a cell or cells, which can be in vitro or in vivo, as desired. In vivo administration can be achieved as described herein or as otherwise known to those of ordinary skill. For in vitro use, delivery of the active agent(s) can be carried out by adding the composition (e.g., liposome or complex) to the cell culture medium, for example.

Pharmaceutical compositions of the present invention can be administered by any route, including but not limited to administration intravenously, subcutaneously, orally or parenterally, intraperitoneally, topically, dermally, rectally, and vaginally.

The use of terms "a" and "an" and "the" and similar referents in the context of describing the invention (especially in the context of the following claims) are to be construed to cover both the singular and the plural, unless otherwise indicated herein or clearly contradicted by context. The terms "comprising", "including", "having", and "containing" are to be construed as open-ended terms (i.e. meaning "including but not limited to") unless otherwise noted. The use of any and all examples, or exemplary language (e.g., "such as") provided herein, is intended merely to better illuminate the invention and does not pose a limitation on the scope of the invention unless otherwise claimed. No language in the specifications should be constructed as indicating any non-claimed element as essential to the practice of the invention.

Preferred embodiments of this invention are described, including the best mode known to the inventors for carrying out the invention. Variations of those preferred embodiments can become apparent to those of ordinary skilled artisans to employ such variations as appropriate, and the inventors intend for the inventions to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patent cited herein, including those in the list below and otherwise cited in this specification, are hereby incorporated by reference in their entireties, to the same extent as if each reference was individually and specifically indicated to be incorporated by reference and were set forth in the entirely herein.

The following examples further illustrate the invention but, of course, should not be construed as in any way as limiting its scope.

EXAMPLE 1

Synthesis of E-Guggulsterol, Z-Guggulsterol or a Mixture of E- and Z-Guggulsterol

IIA

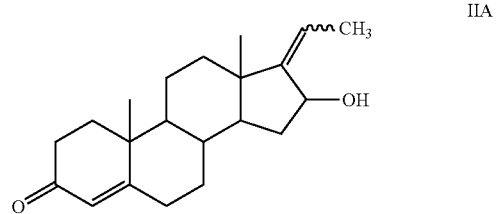

Figure 3:
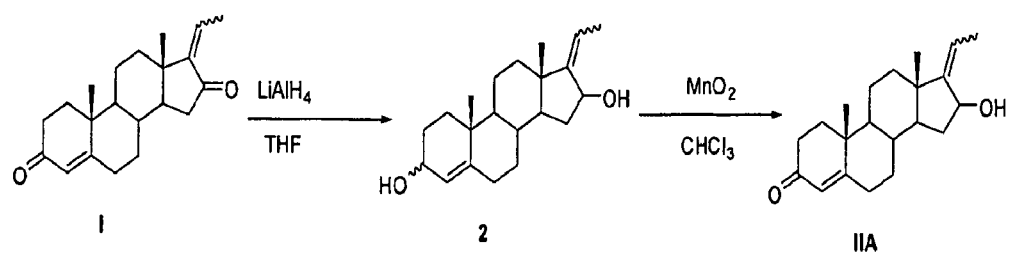

This Example demonstrates a fast and convenient methods for the synthesis of E-Guggulsterol and Z-Guggulsterol or a mixture of E- and Z-Guggulsterol (II A) from commercially available E-Guggulsterone and Z-Guggulsterone or mixture of E- and Z-Guggulsterone (I). Compound (IIA) can be synthesized via a synthetic route outlined in FIG. 3.

Guggulsterone (I) (5.0 g, 16.02 mmol) was dissolved in anhydrous tetrahydrofuran (THF) (50 ml) and added dropwise to a slurry of lithium aluminum hydride (LiAlH$_4$) (1.0 g, 26.35 mmol) in anhydrous THF (100 ml) over a period of 30 minutes, maintaining the temperature between 20° C. to 25° C. After the mixture was stirred for 3 hours, the progress of reaction was checked by TLC (hexane:ethyl Acetate; 6: 4, v/v). After completion of reaction, the excess of LiAlH$_4$ was destroyed by adding ice-cold water in small portion. The organic layer was washed with ice-cold water, dried over anhydrous sulfate, filtered, and evaporated in vacuo to yield 4, 17(20)-Pregnadiene-3β,16α-diol of the formula (2) (4.73 g).

The compound of formula (2) was dissolved in anhydrous methylene chloride (60 ml) and activated manganese(IV) oxide(MnO$_2$)(10.0 g; 115.02 mmole) was added and stirred at room temperature for 1.0 hour and then heated to 40° C. with stirring for 30 minutes, followed by stirring additional 8.0 hours at room temperature. Progress of reaction was checked by TLC (methylene chloride:acetone; 9:1, v/v). After the reaction was completed, the excessive manganese oxide was filtered through celite pad under vacuum. The solvent was removed in vacuo to give the crude product as yellow viscous oil (3.66 g). The crude product was purified over silica gel column by eluting first with methylene chloride followed by 2% acetone in methylene chloride. The fractions containing the pure product were pooled and concentrated in vacuo. The solid obtained was recrystallized in methylene chloride/hexane (1:10, 20 ml) to give a white solid of the title compound (II A) (1.67 g; Yield 33.2%).

EXAMPLE 2

Preparation of Guggulsteryl Sulfate (VII)

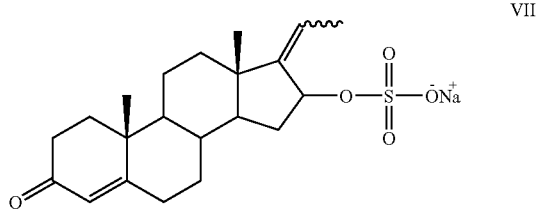

Figure 4:
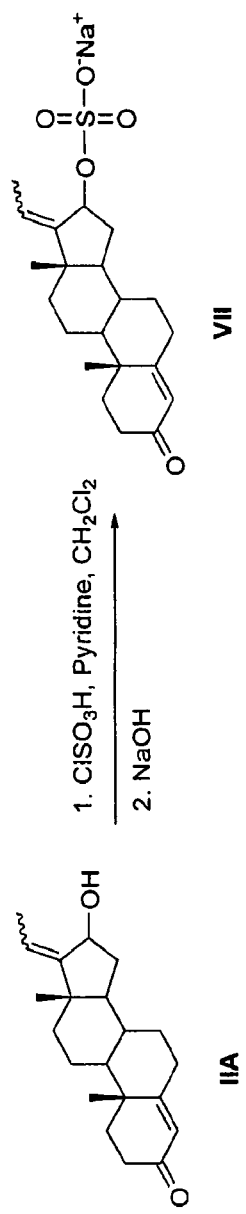
FIG. 4 diagrams an exemplary synthetic scheme for compound VII.

This example demonstrates a method for preparing Guggulsteryl sulfate (VII) from E-guggulsterol and Z-guggulsterol or mixture of E and Z-guggulsterols (II A). The compound VII can be synthesized via the synthetic route outlined in FIG. 4. To a solution of anhydrous pyridine (5 ml) and anhydrous methylene chloride (5 ml) under nitrogen, chlorosulfonic acid (0.5 ml) was added and stirred in an ice-water bath for 15 minutes. Guggulsterols (IIA) (0.108 g, 0.343 mmol) was dissolved in anhydrous methylene chloride (5 ml) and added to the solution of pyridine-chlorosulfonate with stirring. The reaction mixture was stirred vigorously for 15 minutes in an ice-water bath. The ice-water bath was then removed and the reaction mixture was allowed to warm to room temperature. The reaction flask was then refluxed for 3 hours. The solvents were removed in vacuo to give a white solid, which was converted to sodium salt by adding 0.1 NaOH followed by drying under high vacuum. The purity of the product was checked by TLC (methylene chloride:acetone; 9:1 v/v). The crude solids were triturated with diethyl ether (25 ml×2) to remove impurities and then precipitated in methanol and filtered to provide the title compound (VII) (0.060 g; yield 41.95%).

EXAMPLE 3

Preparation of Guggulmyristate

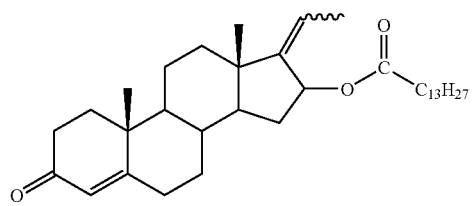

Figure 5:
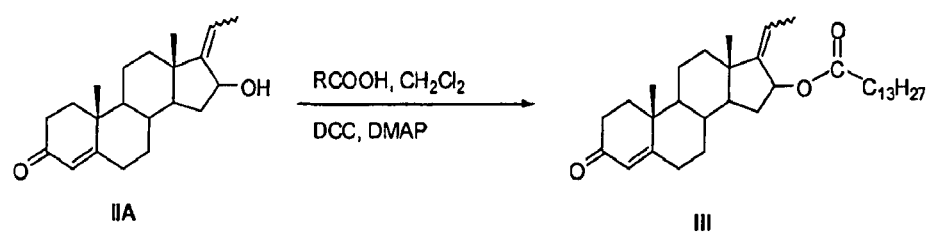
FIG. 5 diagrams an exemplary synthetic scheme for compound III.

This example demonstrates a method for preparing Guggulmyristate, a specific example of compound III, from E-guggulsterol and Z-guggulsterol or a mixture of E- and Z-guggulsterols (II A). Compound III can be synthesized via the synthetic route outlined in FIG. 5. To a stirred solution of guggulsterols (IIA)(0.109 g, 0.348 mmol) in anhydrous methylene chloride (15 ml) was added N,N'-dicyclohexylcarbodiimide(DCC) (1.58 g; 7.65 mmol), followed by myristic acid (C14:0) (0.1873 g; 0.820 mmol) and catalytic amount of 4-dimethylaminopyridine (DMAP) (0.05 g; 0.409 mmol). The reaction mixture was stirred overnight at room temperature. The progress of reaction was monitored by TLC (hexane:ethyl acetate, 6:4, v/v). After completion of reaction, the resulting white precipitate of DCU was filtered and washed with methylene chloride. The solvent was removed using a rotary evaporator to yield white solids (2.01 g). The crude product was purified over silica gel column (40 g) by eluting first with hexane (200 ml) and then with hexane:ethyl acetate (90:10; v/v). The fractions containing pure product were pooled and filtered through a 0.2 μm acrodisc. The solvents were removed in vacuo and dried under high vacuum to give the title compound III (0.16 g; yield 87.6%).

EXAMPLE 4

Preparation of Guggulphosphatidic Acid (Vi)

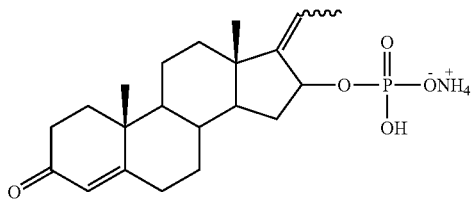

Figure 6:
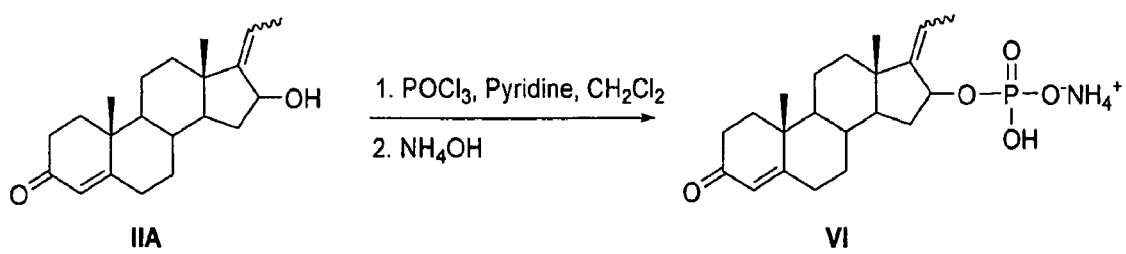
FIG. 6 diagrams an exemplary synthetic scheme for compound VI.

This example demonstrates a method for preparing Guggulphosphatidic acid (VI) from E-guggulsterol and Z-guggulsterol or a mixture of E and Z-guggulsterols (IIA). Compound VI can be synthesized via the synthetic route outlined in FIG. 6. Guggulsterol (IIA) (0.150 g; 0.477 mmol) was dissolved in anhydrous pyridine (10 ml) under nitrogen, and phosphorus oxychloride [POCl$_3$] (2 ml) was added drop wise and reaction mixture was stirred at room temperature for 30 minutes, after which the reaction mixture was refluxed for 2 hours. The reaction mixture was then cooled to room temperature and pyridine was removed using a rotary evaporator. The residue was dissolved in chloroform (25 ml) and washed with water (50 ml×3), dried over anhydrous sodium sulfate, and filtered. Ammonium hydroxide (2 ml) was added to the filtrate and the solvent was removed in vacuo. The crude product was precipitated in methylene chloride:acetone (1:10) at −20° C., filtered and dried under high vacuum to give the title compound VI (53 mg; yield 26.9%).

EXAMPLE 5

Preparation of Guggulphospholipid (V)

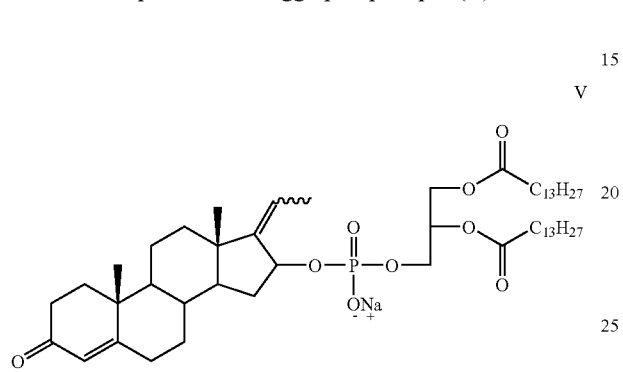

Figure 7:
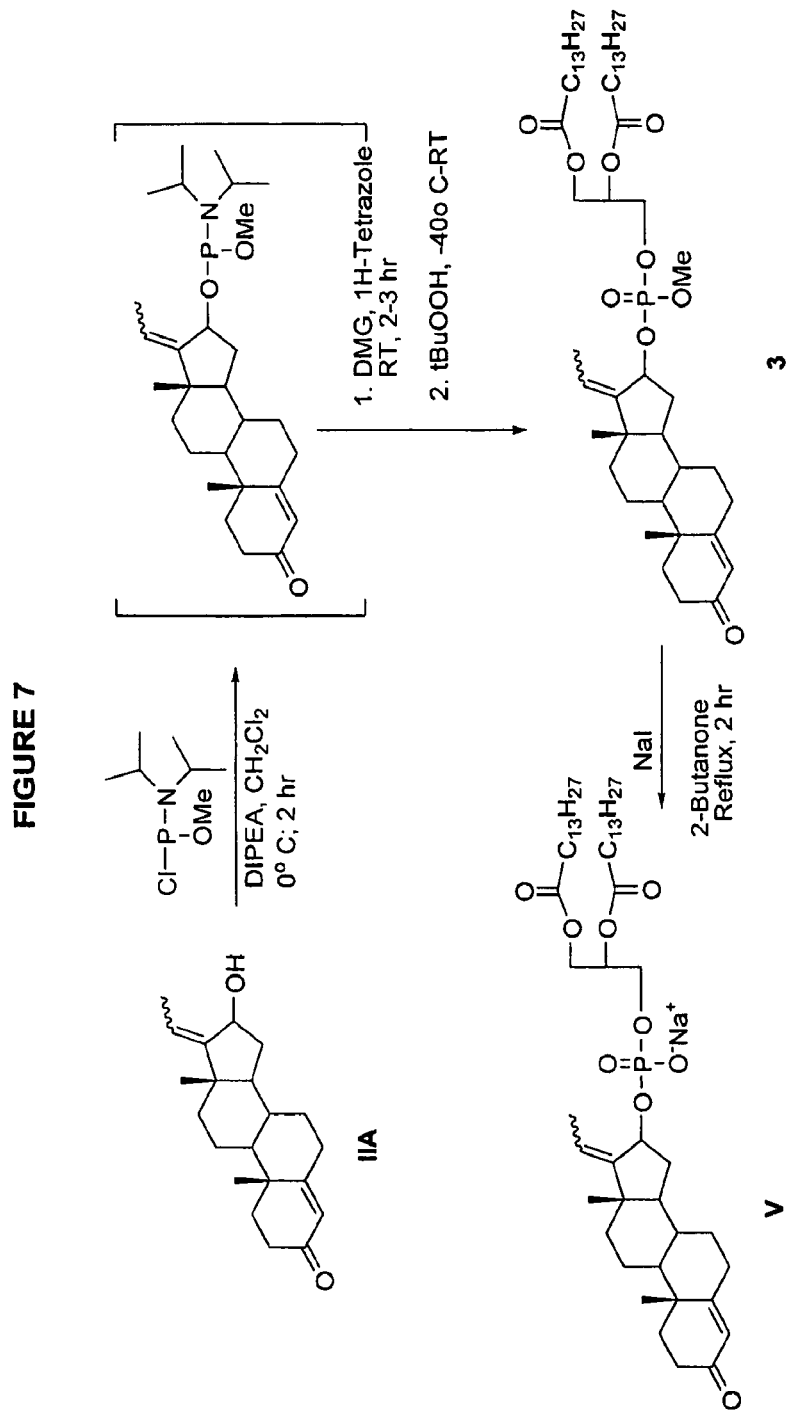
FIG. 7 diagrams an exemplary synthetic scheme for compound V.

This example demonstrates a method for preparing Guggulphospholipid (V) from E-guggulsterol and Z-guggulsterol or mixture of E and Z-guggulsterols (IIA). Compound V can be synthesized via the synthetic route outlined in FIG. 7. To a solution of Guggulsterols IIA (0.100 g; 0.318 mmol) in anhydrous methylene chloride (5 ml) at 0° C.; N,N-diisopropylethylamine (DIPEA) (1.0 ml; 5.71 mmol) and N,N-diisopropylmethylphosphonamidic chloride (1.0 ml; 5.18 mmol) were sequentially added drop wise while maintaining the temperature between 0° C.-5° C. The reaction mixture was stirred for 6 hours at 0° C. and the progress of reaction was monitored by TLC (methylene chloride:acetone; 9:1). After complete consumption of Guggulsterols IIA, the ice-bath was removed and the mixture was gradually allowed to attain room temperature. Tetrazole solution (0.45M in acetonitrile) (1.0 ml) was added followed by 1,2-dimyristoylglycerol (0.16 g; 0.312 mmol), and the reaction mixture was stirred at room temperature for 24 hours. The reaction mixture was then cooled to −40° C., tert-butylhydroperoxide (1 ml) was added, and the mixture was stirred for 1 hour. The reaction mixture was gradually allowed to attain room temperature and stirring was continued for additional 1 hour at room temperature. The contents were diluted with methylene chloride (50 ml) and the organic layer was washed successively with ice-cold 5% HCl (10 ml×2), aq. sodium bicarbonate (50 ml×2), water (50 ml) and brine (50 ml), dried over anhydrous sodium sulfate and concentrated. The resulting intermediate 3 was dried under high vacuum to give yellow viscous oil (1.16 g). The resulting oil was purified over silica gel column (15 g) eluting with 1% methanol in methylene chloride to produce the intermediate 3 (0.52 g).

To a stirred solution of the intermediate 3 (0.50 g; 0.553 mmol) in 2-butanone (20 ml) was added sodium iodide (0.250 g, 1.66 mmole), and the reaction mixture was refluxed for 2.5 hours and cooled to 25° C. and then at −20° C. overnight. The sodium salt of title compound V was filtered and washed with chilled acetone to give 0.22 g (76.12%) as white solid.

EXAMPLE 6

Synthesis of Guggulphospholipid (V)

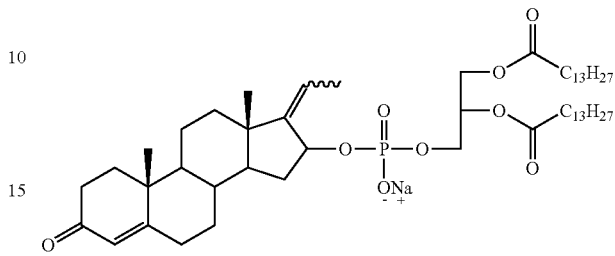

Figure 8:
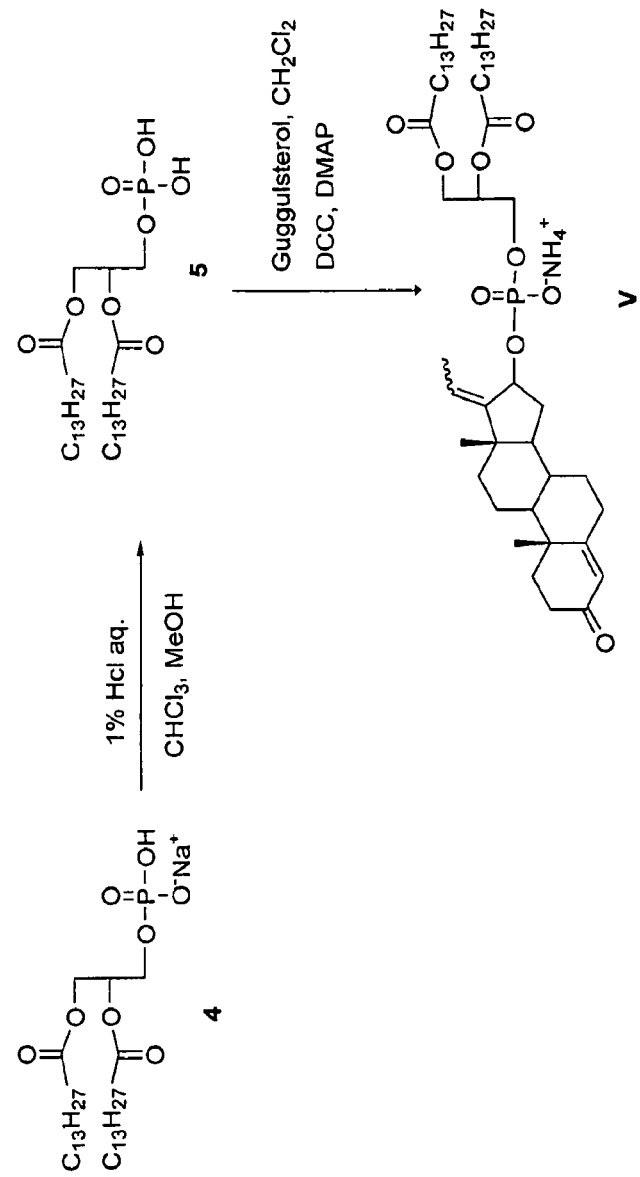
FIG. 8 diagrams an exemplary synthetic scheme for compound V.

This example demonstrates a second approach for the synthesis of Guggulphospholipid V from E-guggulsterol and Z-guggulsterol or mixture of E- and Z-guggulsterols (IIA). Another approach for the synthesis of compound V is outlined in FIG. 8. The 1,2-dimyristoyl-sn-glycero-3-phosphatidic acid sodium salt (4) (200 mg) was dissolved in chloroform:methanol (8:2, v/v) and was converted to its free acid form by washing with ice-cold 0.1N HCl, followed by washing with deionized water. The organic layer was dried over anhydrous sodium sulfate and concentrated. The resulting 1,2-dimyristoyl-sn-glycero-3-phosphatidic acid, 5 (DMPA) (190 mg, 0.320 mmol) was dried under high vacuum over $P_2O_5$ overnight before use.

To a stirred solution of guggulsterols (IIA) (100 mg; 0.318 mmole) in anhydrous methylene chloride (15 ml) N,N'-dicyclohexylcarbodiimide (DCC) (1.5 g; 7.6576 mmol) was added and stirred at room temperature for 5 minutes. Compound 5 (DMPA) dissolved in anhydrous methylene chloride (5 ml) was added to reaction mixture, followed by a catalytic amount of 4-dimethylaminopyridine (DMAP) (25 mg). The reaction mixture was stirred overnight at room temperature. The progress of reaction was monitored by TLC (methylene chloride:acetone; 9:1, v/v). After completion of reaction, the resulting white precipitate of DCU was filtered and washed with methylene chloride. The solvent was removed in vacuo to yield viscous oily material (1.19 g). The crude product was purified over silica gel column (20 g) packed in $CHCl_3$: $MeOH:NH_4OH$ (75:20:5, v/v), and the column was eluted in the same solvent system. The fractions containing pure product were pooled and filtered through a 0.2 μm acrodisc. The solvent was removed using a rotary evaporator and dried under high vacuum to give the ammonia salt of the title compound V (115 mg; yield 60.8%).

EXAMPLE 7

Preparation of Guggulphosphocholine (VIII)

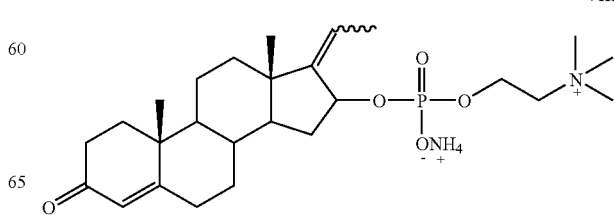

Figure 9:
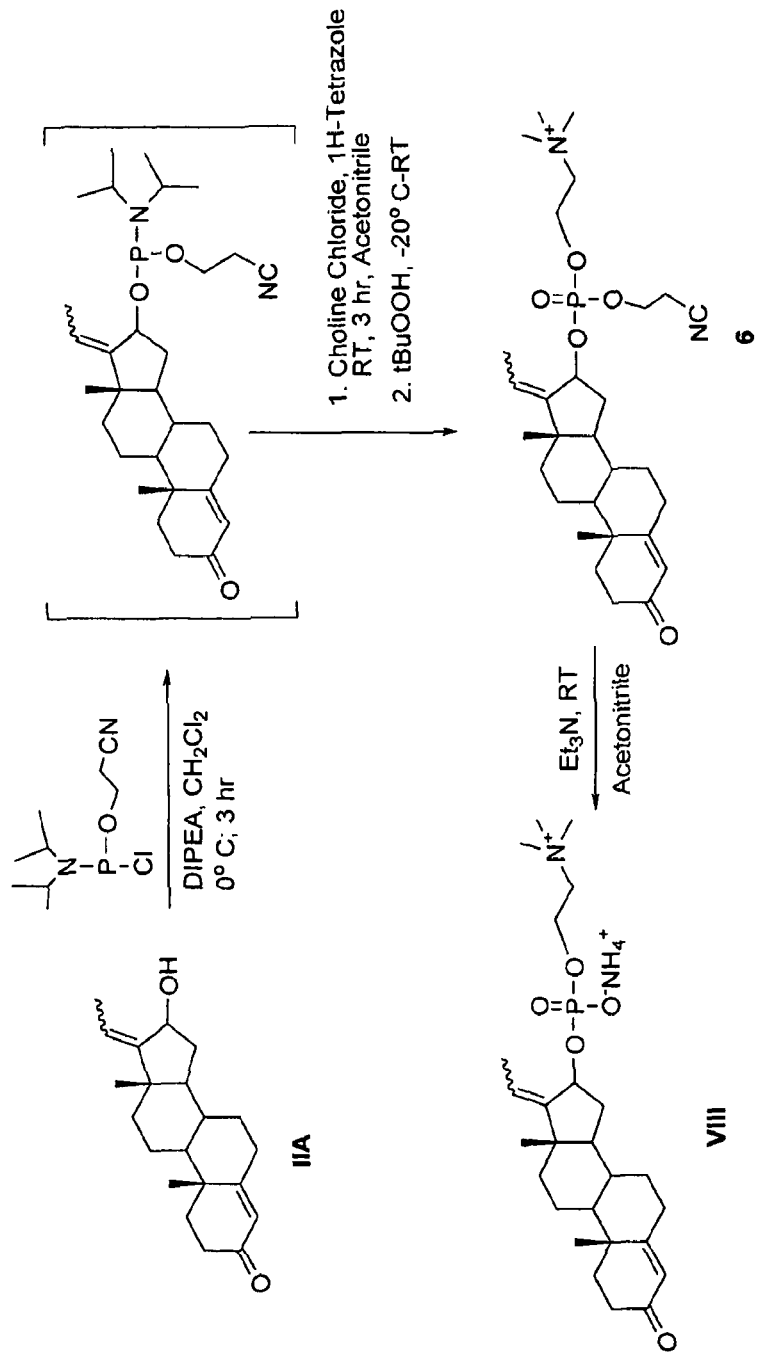
FIG. 9 diagrams an exemplary synthetic scheme for compound VIII.

This example demonstrates a method for preparing Guggulphosphocholine (VIII) from E-guggulsterol and Z-guggulsterol or a mixture of E and Z-guggulsterols (IIA). Compound VIII can be synthesized via the synthetic route outlined in FIG. 9. To a solution of guggulsterols IIA (0.150 g; 0.477 mmol) in anhydrous methylene chloride (10 ml) at 0° C.; N,N diisopropylethylamine (DIPEA) (100 µl) and 2-cyanoethyldiisopropylchlorophosphoramidite (120 µl) were sequentially added at 0° C. The reaction mixture was stirred for 3 hours at 0° C. The progress of reaction was monitored by TLC (methylene chloride:acetone; 9:1). After complete consumption of guggulsterols IIA, the ice-bath was removed and the mixture was gradually allowed to attain room temperature. Tetrazole solution (0.45M in acetonitrile) (5.0 ml) was added, followed by choline chloride (0.075 g; 0.537 mmol), and the reaction mixture was stirred at room temperature for 24 hours. The reaction mixture was then cooled to −20° C. and tert-butylhydroperoxide (100 µl) was added and stirred for 1 hour at this temperature and gradually allowed to attain room temperature and continued stirring for additional 1 hour at room temperature. The contents were diluted with methylene chloride (50 ml) and the organic layer was washed successively with ice-cold 5% HCl (10 ml×2), aq. sodium bicarbonate (50 ml×2), water (50 ml) and brine (50 ml), dried over anhydrous sodium sulfate, and concentrated. The resulting intermediate 6 was dried under high vacuum to give a semisolid (1.02 g). A solution of the above intermediate 6 in acetonitrile (10 ml) was mixed with triethylamine (Et$_3$N) (1 ml) and stirred at room temperature for 24 hours. The contents were concentrated and purified by flash column chromatography with CHCl$_3$:MeOH:NH$_4$OH (75:20:5, v/v) as eluent to produce the ammonia salt of title compound VIII as a white solid (0.11 g, 43.2%).

EXAMPLE 8

Particles Comprising Tacrolimus, Guggulsterol, and Soy Lecithin

Tacrolimus (20 mg), Guggulsterol (8 mg), and Soy lecithin (792 mg) were mixed together in water (15 mL) and homogenized for 10 minutes. The suspension was sonicated at 45° C. for 10 minutes and then passes through high pressure homogenizer. The resulting suspension was then mixed with 7.5% sucrose solution (5 mL) and lyophilized. The particle size was determined using Nicomp particle sizer 380. The mean particle diameter amounted to less than 200 nm.

| Mean/Distributions | Particle Size (Volume Weighting) |
|---|---|
| Mean Volume Weighting Diameter | 67.2 nm |
| 99% Distribution | 200.7 nm |
| 90% Distribution | 115.4 nm |
| 80% Distribution | 91.5 nm |
| 75% Distribution | 83.8 nm |
| 50% Distribution | 58.7 nm |
| 25% Distribution | 41.2 nm |

EXAMPLE 9

Particles Comprising Paclitaxel, Guggulsterol, and Soy Lecithin

Paclitaxel (40 mg), Guggulsterol (14.73 mg), and Soy lecithin (1.58 g) were mixed together in water (15 mL) and homogenized for 10 minutes. The suspension was sonicated at 45° C. for 10 minutes and then passes through high pressure homogenizer. The resulting suspension was then mixed with 7.5% sucrose solution (5 mL) and lyophilized. The particle size was determined using Nicomp particle sizer 380. The mean particle diameter amounted to less than 200 nm.

| Mean/Distributions | Particle Size (Volume Weighting) |
|---|---|
| Mean Volume Weighting Diameter | 106.6 nm |
| 99% Distribution | 62.0 nm |
| 90% Distribution | 90.9 nm |
| 80% Distribution | 133.8 nm |
| 75% Distribution | 189.6 nm |
| 50% Distribution | 346.2 nm |
| 25% Distribution | 147.2 nm |

REFERENCES

1. Bruzik, K. S.; Kubiak, R. J. *Tet. Lett.* 1995, 36, 2415-2418.
2. Prestwich, G. D.; Marecak, J. F.; Mourey, R. J.; Thiebert, A. B.; Ferris, C. D.; Danoff, S. K.; Snyder, S. H. *J. Am. Chem. Soc.* 1991, 113, 1822-1825.
3. Dreef, C. E.; Elie, C. J. J.; Hoogerhout, P.; van der Marel, G. A.; van Boom, J. H. *Tetrahedron Lett.* 1988, 29, 6513-6516),
4. Browne, J. E.; Driver, M. J.; Russel, J. C.; Sammes, P. G. *J. Chem. Soc. Perkin Trans.* 1. 2000, 653-657.
5. Chen, J.; Feng, L.; Prestwich, G. D. *J. Org. Chem.* 1998, 63, 6511-6522;
6. Watanabe, Y.; Nakamura, T.; Mitsumoto, H. *Tetrahedron Lett.* 1997, 38, 7407-7410,
7. Murakami, K.; Molitor, E. J.; Liu, H. W. *J. Org. Chem.* 1999, 64, 648-651.
8. Watanabe, Y.; Inada, E.; Jinno, M.; Ozaki, S. *Tetrahedron Lett.* 1993, 34, 497-500.
9. Watanabe, Y.; Ishikawa, H. *Tetrahedron Lett.* 2000, 41, 8509-8512
10. Lindberg, J.; Ekeroth, J.; Konradsson, P. *J. Org. Chem.* 2002, 67, 194-199.
11. Chevallier, J.; Sakai, N.; Robert, F.; Kobayashi, T.; Gruenberg, J.; Matile, S. *Org. Lett.* 2000, 2, 1859-1861.
12. Martin, S. F.; Josey, J. A.; Wong, Y-L.; Dean, D. W. *J. Org. Chem.*, 1994, 59, 4805-4820.
13. Wilk, A.; Srinivasachar, K.; Beaucagem S. *J. Org. Chem.* 1997, 62, 6712-6713.
14. Wissner, A.; Kohler, C. A.; Goldstein, B. M. *J. Med. Chem.* 1986, 29, 1315-1319.
15. Andresen, T. L; Jensen, S. S.; Madsen, R.; Jørgensen, K. *J. Med. Chem.* 2005, 48, 7305-7314.
16. Marx, M. H.; Piantadosi, C.; Noseda, A.; Daniel, L. W.; Modest, E. J. *J. Med. Chem.* 1988, 31, 858-863.
17. Andresen, T. L; Davidsen, J.; Begtrup, M.; Mouritsen, O. G.; Jørgensen, K. *J. Med. Chem.* 2004, 47, 1694-1703.
18. Drummond, D. C,; Meyer, O.; Hong, K.; Kirpotin, D. B.; Papahadjopoulos, D. *Pharm. Rev.,* 1999, 51, 691-743.
19. Hunt, V.; and Wolff, S. P. *Free Radical Res. Commun.* 1991, 12-13, 115.
20. Singh, K.; Chander, R. and Kapoor, N. K. *Phytotherapy Research,* 1997, 11, 2919.
21. Flood, J. F.; Moorley, J. F.; and Robert, E. *Proc. Natl. Acad. Sci. USA* 1992, 89, 1567.

22. Bowlby, M. R. *Mol. Pharmacol.* 1993, 43, 813.
23. Patil, V. D.; Nayak, U. R.; and Sukh Dev *Tetrahedron,* 1972, 28, 2341.
24. Gujral, M. L.; Sareen, K.; Tangri, K. K.; Amma, M. P. K.; and Roy, A. K. *Ind. J Physiol. Pharmacol.* 1960, 4, 267.
25. Nityanand, S, and Kapoor, N. K. *Ind J Exp. Biol.* 1973, 11, 395.
26. Kapoor, N. K.; and Nityanand, S. *Ind. J Heart Res. Supp*-1. 22, 1988.
27. Mc Cook, J. P.; Corey, J. M.; Dorogi, P. L.; Bajor, J. S.; Knaggs, H. E.; Lange, B. A.; Sharpe, E. U.S. Pat. No. 5,690,948 (1997).
28. Satyavati, G. V. *Economic and Medical Plant Research.* 1991, 5, 47.

What is claimed is:
1. A composition comprising a guggul-based lipid molecule having a general structure selected from the group consisting of structures IV-XII

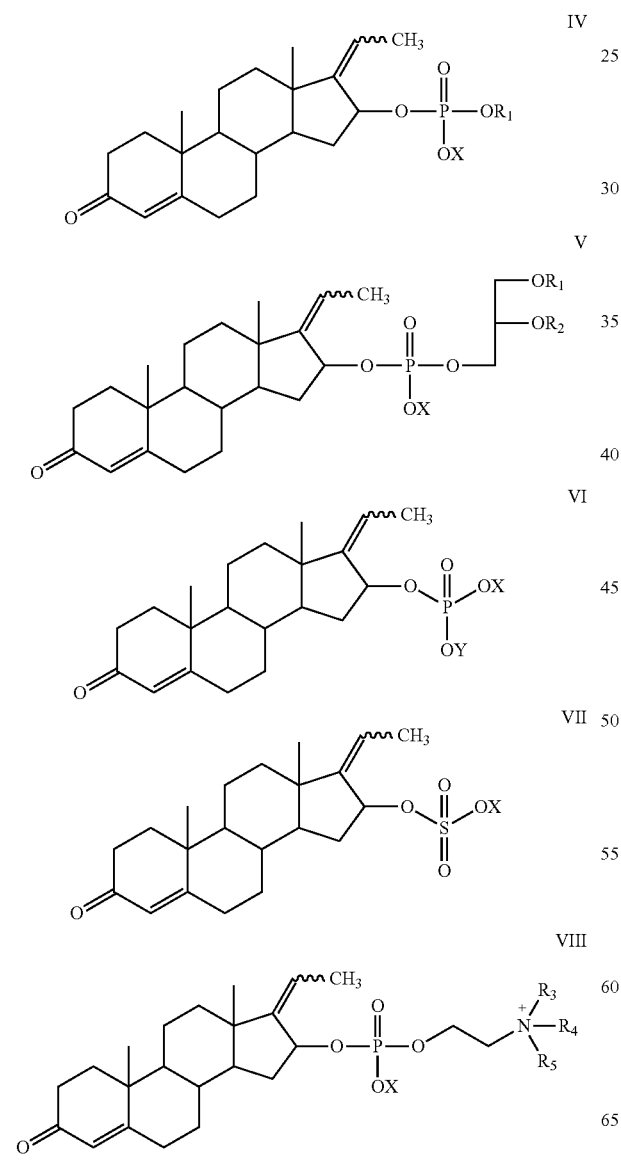
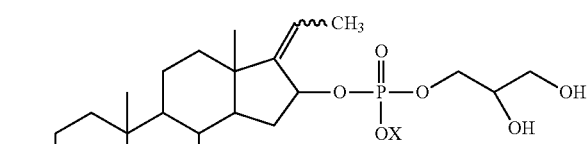
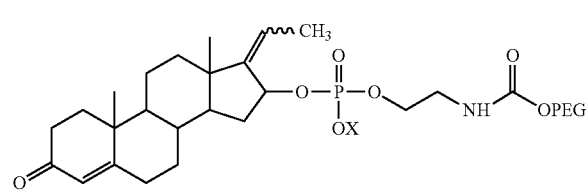
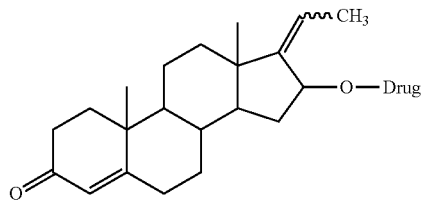
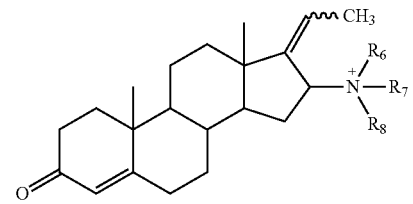

wherein:
i) in structure IV, $R_1$ is a saturated or unsaturated acyl or alkyl groups having between 1 and 34 carbon atoms;
ii) in structure IV, $R_1$ is a saturated alkyl or alkyloxy group optionally substituted with amino or substituted amino group;
iii) in structure IV, $R_1$ is a sugar;
iv) in structure V, $R_1$ and $R_2$ are same or different and at least one of the $R_1$ or $R_2$ is a saturated or unsaturated acyl group or alkyl group having between 1 and 34 carbon atoms;
v) in structures IV-X, X is hydrogen, methyl, ammonium, sodium, potassium, calcium, barium ion or any non-toxic ion;
vi) in structure VI, X and Y are same or different and are hydrogen, methyl, hydrogen, ammonium, sodium, potassium, calcium, barium ion or any non-toxic ion;
vii) in structure VIII, $R_3$, $R_4$ and $R_5$ are same or different and are hydrogen or methyl group; X is hydrogen or methyl group;
viii) in structure X, PEG (polyethylene glycol) is a long chain, linear or branched synthetic polymer composed of ethylene oxide units, $HO(CH_2CH_2O)_n CH_2CH_2OCH_3$, where n is typically between about 1 and about 1000;
ix) in structure XI drug is an active agent; and
x) in structure XII, $R_6$, $R_7$, and $R_8$ are same or different and are selected from a group consisting of hydrogen, methyl, alkyl, substituted alkyl, alkyoxy, substituted alkyloxy groups, and are optionally hydroxylated, aminated, or polyaminated such that the composition has an having overall positive charge, and wherein:

xi) structures IV-XII are in the form selected from the group consisting of E-isomer, Z-isomer, or a mixture of E- and Z-isomers;

xii) structures IV-XII are optically pure, or one or more of structures IV XII are mixtures of optical isomers;

xiii) structure VIII is cationic when X is a methyl group; and xiv) structure XII is cationic.

2. The composition of claim 1, wherein compound XI is prepared by conjugating guggulsterol with a drug directly or through a linker, wherein the linker is an alkyl group optionally substituted with a functional group selected from the groups consisting of carbonyl, carboxyl, carbonate, amino, amide, ester, thioester groups, succinate, glutarate, carbamate, ether, phosphate, phosphonate, diphosphate, and pyrophosphate.

3. The composition of claim 1, further comprising complexing said guggul-based lipid molecule into a composition comprising a liposome or lipid complex, wherein said complex is selected from a group consisting of micelles, vesicles, and emulsions, and wherein, if said composition comprises a plurality of micelles, said micelles are in the form of monomeric, dimeric, polymeric or mixed micelles.

4. The composition of claim 1, comprising a guggul derivative of a formula selected from the group consisting of formula VI-XII, said guggl derivative prepared by reacting a guggulsterone having structure I or a guggulsterol having structure IIA

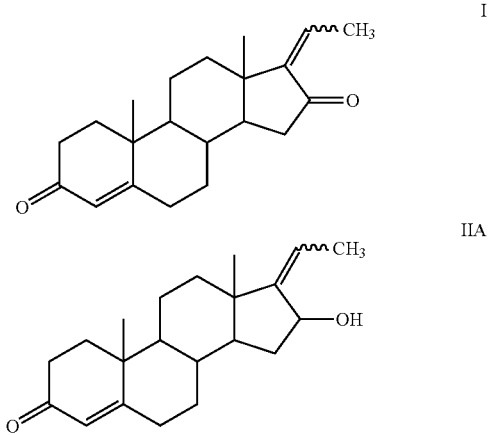

to form a composition comprising a guggul derivative of a formula selected from the group consisting of formula VI-XII.

5. The composition of claim 4, wherein said guggulsterone I and/or said guggulsterol IIA is an E-isomer or Z-isomer or a mixture of E and Z isomers and are optically pure or a mixture of optical isomers.

6. The composition of claim 4, wherein preparation of guggulsterol IIA comprises treating guggulsterone I in one or more steps to produce guggulsterol IIA.

7. The composition of claim 1, wherein said guggul-based lipid molecule has a general structure of formula IV, V, VI, VIII, IX or X, wherein at least one step in preparing said composition comprises the use of a phosphoramidite reagent or a phosphorylating agent selected from a group consisting of N,N-diisopropylmethylphosphoramidic chloride, (benzyloxy)(N,N-diisopropylamino)chlorophosphine, benzyloxybis (diisopropylamino) phosphine, 2-cyanoethyl-N,N,N,N-tetraisopropylphosphoramidite, (2-cyanoethyl)(N,N-diisopropylamino)chlorophosphine, difluorenyl diisopropylphosphoramidite, methyl-N,N,N,N tetraisopropylphosphorodiamidite, dimethyl N,N-diisopropylphosphoramidite, dibenzyl diisopropylphosphoramidite, di-tert-butyl-N,N-diisopropylphosphoramidite, 2-(diphenylmethylsilyl)ethyl-N,N,N,N-tetraisopropylphosphoramidite, (N-trifluoroacetylamino) butyl and (N-trifluoroacetylamino) pentyl-N,N,N,N-tetraisopropylphosphoramidites, 2-bromoethyldichlorophosphate, trimethylsilylethyl dichlorophosphate, methyl dichlorophosphate, 2-chloro-2-oxo-1,3,2-dioxaphospholane, 2-chlorophenyl dichlorophosphate, and phosphorus oxychloride.

8. The composition of claim 3, wherein said composition further comprises a phospholipid selected from a group consisting of a phosphatidylcholine, a phosphatidylethanolamine, a phosphatidylglycerol, a phosphatidylserine, a phosphatidylinositol, a phosphatidic acid; a pegylated phospholipid selected from a group consisting of a pegylated derivative of disteroylphosphatidylglycerol, dimyristoylphosphatidylglycerol, or dioleoylphosphtidylglycerol; polyethylene glycol (PEG) having an average molecular weight of 200-20,000; a saturated or unsaturated fatty acid selected from a group consisting of fatty acids having chain length of $C_4$-$C_{34}$; a fatty acid in acidic form or in salt form; a sterol selected from a group consisting of cholesterol, a derivative of cholesterol, cholesteryl sulfate, cholesterol succinate, cholesterol hemisuccinate, cholesterol oleate, cortisol, corticosterone, hydrocortisone, cholesterol-PEG, coprostanol, cholestanol, cholestane, β-sitosterol, lanosterol, campesterol, lathosterol, stigmasterol, stigmastanol, calciferol, a guggulsterol, and a derivative of a guggulsterol; sodium deoxycholate, α-tocopherol, and mixtures thereof.

9. The composition of claim 3, wherein said drug comprises at least one therapeutically active agent, wherein said at least one therapeutically active agent comprises an anti-cancer drug, an antiviral drug, antibacterial drug, an antifungal drug, an anti-inflammation drug, or a cholesterol lowering drug, and wherein said at least one therapeutically active agent is selected to treat cardiovascular disease, to treat neoplasia, to improve memory loss to treat skin infection or skin disease, to treat hyperglycemia, or to enhance cognitive function.

10. The composition according to claim 1 or claim 3, wherein said composition is in lyophilized form, wherein said lyophilized form comprises a cryoprotectant, wherein said cryoprotectant comprises one or more sugars selected from a group consisting of trehalose, maltose, lactose, sucrose, and dextran.

11. The composition according to claim 3, wherein said composition comprising said liposome or lipid complex comprises a form selected from the group consisting of a powder, a solution, a suspension, in an emulsion, a gel, a micelle, a paste, a tablet, and a capsule, wherein said tablet and said capsule are with or without enteric coating.

12. A method of transfecting a cell with a polynucleotide, comprising (a) preparing a composition comprising a cationic guggul derivative of claim 1, said guggul derivative having a general structure selected from the group consisting of structures VIII and XII, and said polynucleotide; and (b) contacting said cell with said composition, whereby said polynucleotide is taken up by the cell, wherein said polynucleotide is selected from a group consisting of oligonucleotides comprising DNA, RNA, or DNA and RNA, antisense oligonucleotudes, small interfering RNAs (siRNAs), microRNAs (miRNAs), aptamers, and ribozymes, and wherein and said polynucleotide is a single-stranded, double-stranded, or partially single stranded and partially double stranded.

13. A method of treating a cell, comprising providing a composition comprising a guggul-based lipid molecule of claim 1, and exposing said cell to said composition.

14. A kit for transfecting cells, said kit comprising a composition comprising a cationic guggul derivative of a guggul-based lipid molecule of claim 1 and one or more elements selected from the group consisting of a polynucleotide, instructions for formulating the cationic guggul derivative and polynucleotide into a preparation, instructions for transfecting cells using the cationic guggul derivative, reagents for facilitating transfection, containers for storing the cationic guggul derivative, containers for storing the polynucleotide, containers for storing the reagents, containers for storing a preparation including the cationic guggul derivative and polynucleotide, or containers for preparing the preparation, and materials to facilitate transfection.

* * * * *